(12) United States Patent
Miller et al.

(10) Patent No.: US 7,470,703 B1
(45) Date of Patent: Dec. 30, 2008

(54) YOHIMBINE DERIVATIVES AND USE THEREOF

(75) Inventors: Duane D. Miller, Germantown, TN (US); Bob M. Moore, II, Nesbit, MS (US); Suni Mustafa, Memphis, TN (US); Dennis R. Feller, Oxford, MS (US); Supriya A. Bavadekar, Memphis, TN (US)

(73) Assignees: The University of Tennessee Research Foundation, Knoxville, TN (US); The University of Mississippi, University, MS (US)

( * ) Notice: Subject to any disclaimer, the term of this patent is extended or adjusted under 35 U.S.C. 154(b) by 22 days.

(21) Appl. No.: 11/210,206

(22) Filed: Aug. 23, 2005

Related U.S. Application Data

(60) Provisional application No. 60/603,584, filed on Aug. 23, 2004.

(51) Int. Cl.
*A61K 31/4745* (2006.01)
*C07D 471/16* (2006.01)

(52) U.S. Cl. .......................... 514/280; 546/53; 546/50; 435/7.2

(58) Field of Classification Search ................. 514/280; 546/53, 50; 435/7.2
See application file for complete search history.

(56) References Cited

U.S. PATENT DOCUMENTS 3,940,387 A  2/1976  Saint-Ruf et al.
6,638,943 B2 10/2003  Miller et al.

OTHER PUBLICATIONS

Dossin, O. et al.: Characterization of a new radioiodinated probe for the alpha2C adrenoceptor in the mouse brain. Neurochem. Int. vol. 36, pp. 7-18, 2000.*
Lanier, S. M. et al.: Synthesis and characterization of a high affinity radioiodinated probe for the alpha2-adrenergic receptor. Molecular Pharmacol. vol. 29, pp. 219-227, 1986.*
Zheng et al., "Yohimbine Dimers Exhibiting Binding Selectivities for Human $\alpha_{2a}$-versus $\alpha_{2b}$-Adrenergic Receptors," *Biorg. Med. Chem. Lett.* 10:627-630 (2000).
Portoghese et al., "Stereostructure-Activity Relationship of Opioid Agonist and Antagonist Bivalent Ligands. Evidence for Bridging between Vicinal Opioid Receptors," *J. Med. Chem.* 28(9):1140-1141 (1985).
Erez et al., "Narcotic Antagonistic Potency of Bivalent Ligands Which Contain β-Naltrexamine. Evidence for Bridging between Proximal Recognition Sites," *J. Med. Chem.* 25(7):847-849 (1982).
Portoghese, P.S., "The Role of Concepts in Structure-Activity Relationship Studies of Opioid Ligands," *J. Med. Chem.* 35(11):1927-1937 (1992).
Portoghese et al., "Bivalent Ligands and the Message-Address Concept in the Design of Selective Opioid Receptor Antagonists," *TIPS Review* 10:230-235 (1989).
Shimohigashi et al., "Dimeric Tetrapeptide Enkephalins Display Extraordinary Selectivity for the δ Opiate Receptor," *Nature* 297:333-335 (1982).
LeBoulluec et al., "Bivalent Indoles Exhibiting Serotonergic Binding Affinity," *Bioorganic & Medicinal Chemistry Letters* 5(2):123-126 (1995).
Cwirla et al., "Peptide Agonist of the Thrombopoietin Receptor as Potent as the Natural Cytokine," *Science* 276:1696-1699 (1997).
Uhlén et al., "Membrane Organization and Mobility of $\alpha_2$ Adrenergic Receptors in MDCK Cells," *Pharmacology Communications* 6(1-3):155-167 (1995).
Maggio et al., "Coexpression Studies with Mutant Muscarinic/Adrenergic Receptors Provide Evidence for Intermolecular "Cross-Talk" between G-Protein-Linked Receptors," *Proc. Natl. Acad. Sci. USA* 90:3103-3107 (1993).
Maggio et al., "Functional Role of the Third Cytoplasmic Loop in Muscarinic Receptor Dimerization," *J. Biol. Chem.* 271(49):31055-31060 (1996).
Pigini et al., "Imidazoline Receptors: Qualitative Structure-Activity Relationships and Discovery of Tracizoline and Benazoline. Two Ligands with High Affinity and Unprecedented Selectivity," *Bioorganic & Medicinal Chemistry* 5(5):833-841 (1997).
Pigini et al., "Structure-Activity Relationship at α-Adrenergic Receptors Within a Series of Imidazoline Analogues of Cirazoline," *Bioorganic & Medicinal Chemistry* 8:883-888 (2000).
Gentili et al., "$\alpha_2$-Adrenoreceptors Profile Modulation and High Antinociceptive Activity of (S)-(-)-2-[1-(Biphenyl-2-yloxy)ethyl]-4,5-dihydro-1H-imidazole," *J. Med. Chem.* 45:32-40 (2002).
Gentili et al., "Imidazoline Binding Sites (IBS) Profile Modulation: Key Role of the Bridge in Determining $I_1$-IBS or $I_2$IBS Selectivity within a Series of 2-Phenoxymethylimidazoline Analogues," *J. Med. Chem.* 46:2169-2176 (2003).
Gentili et al., "$\alpha_2$-Adrenoreceptors Profile Modulation. 2. [1] Biphenyline Analogues as Tools for Selective Activation of the $\alpha_{2C}$-Subtype," *J. Med. Chem.* 47:6160-6173 (2004).
Lalchandani et al., "Yohimbine Dimers Exhibiting Selectivity for the Human $\alpha_{2C}$-Adrenoceptor Subtype," *The Journal of Pharmacology and Experimental Therapeutics* 303(3):979-984 (2002).
Bavadekar et al., American Chemical Society 2004 Meeting (2004), abstract 60.
Bavadekar et al., "Monomeric Yohimbine Analogs as Selective Human Alpha 2C-Adrenergic Receptor Ligands," *Experimental Biology 2004* Abstract #164.10 (2004).
Mustafa et al., "Synthesis and Biological Studies of Yohimbine Derivatives on Human $\alpha_{2C}$-Adrenergic Receptors," *Bioorganic & Medicinal Chemistry Letters* 15:2758-2760 (2005).

* cited by examiner

*Primary Examiner*—Charanjit S Aulakh
(74) *Attorney, Agent, or Firm*—Nixon Peabody LLP

(57) ABSTRACT

Yohimbine derivatives are disclosed having modification of the C-16 carboxyl group to include a sidechain and where the resulting derivative does not possess a second yohimbine pharmacophore (i.e., the compound is not a yohimbine dimer). The yohimbine derivatives of the present invention are preferably characterized by selective activity as $\alpha_{2C}$-AR antagonists. Use of the compounds, or pharmaceutical composition containing them, for treating or preventing an $\alpha_{2c}$ adrenergic receptor mediated condition or disorder, and for antagonizing activity of an $\alpha_{2c}$ adrenergic receptor are also disclosed.

22 Claims, 9 Drawing Sheets

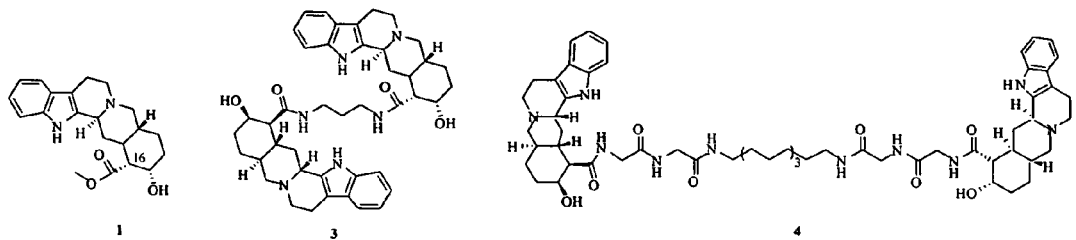

Figure 1

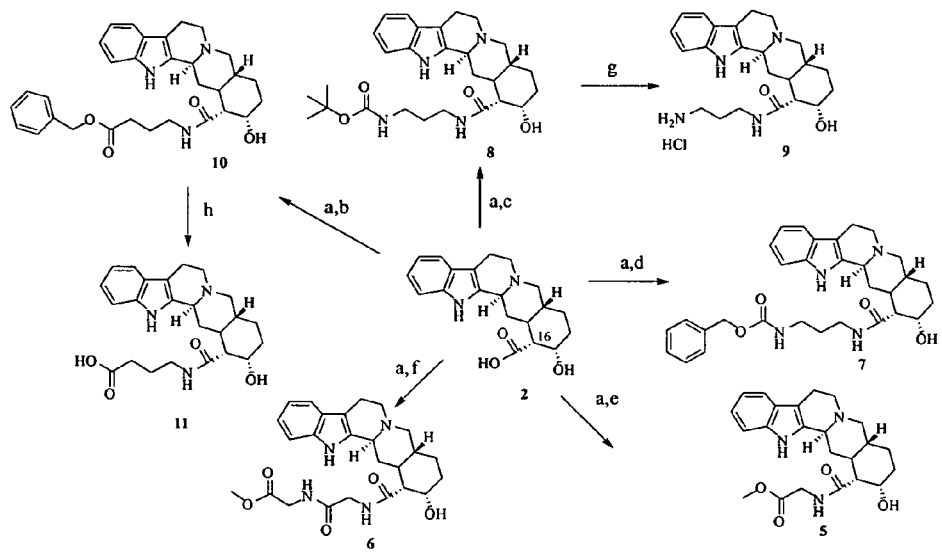

Scheme 1. Reagents and conditions : (a) DCC, HOBT, THF, Et$_3$N, rt; (b) NH$_2$(CH$_2$)$_3$COOBz; (c) NH$_2$(CH$_2$)$_3$NHBoc 16; (d) NH$_2$(CH$_2$)$_3$NHCbz 17; (e) NH$_2$CH$_2$COOMe 18; (f) NH$_2$CH$_2$CONHCH$_2$COOMe 21; (g) HCl in ether,30 min.; (h) H$_2$, 10 %Pd/C, EtOAc. [ Compound 13, the diazidopropane is a very dangerous explosion hazard and it should be handled carefully]

Figure 2A

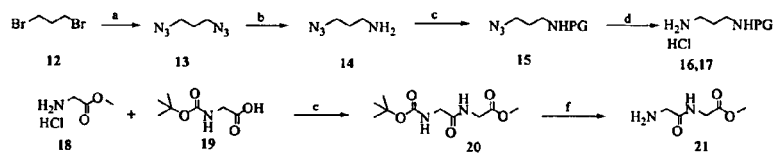

Scheme 2. Reagents and conditions:(a) NaN$_3$, DMF/H$_2$O, 80°C,20h; (b) Ph$_3$P, Et$_2$O/EtOAc-5%HCl, rt,24 h; (c) (Boc)$_2$O/CbzCl, NaOH,THF-H$_2$O, rt; (d) Ph$_3$P, THF, rt, 24 h; PG=Boc, Cbz;(e) EDC, HOBT, Et$_3$N, DCM;(f)TFA,THF,O°C.

Figure 2B

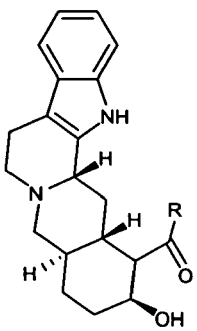
|  | R = |
|---|---|
| Yohimbine (1) |  |
| Yohimbinic acid (2) |  |
| Yoh. monoglycine ester (5) | 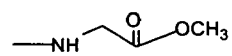 |
| Yoh. diglycine ester (6) | 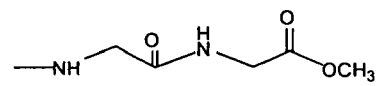 |
| Yoh. benzyl carbamate alkyl amine (7) | 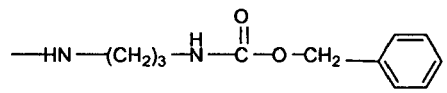 |
| Yoh. t-butyl carbamate alkyl amine (8) | 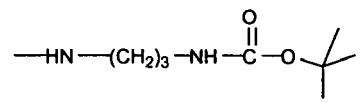 |
| Yoh. alkyl amine (9) | 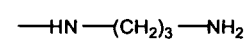 |
| Yoh. benzyl carboxy alkyl amine (10) | 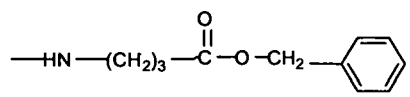 |
| Yoh. carboxy alkyl amine (11) | 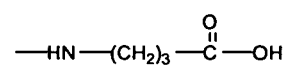 |
Figure 3A

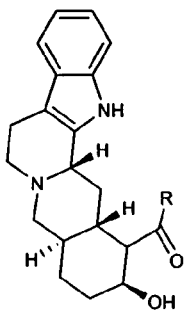
|  | R = |
|---|---|
| Yoh. benzylurea alkyl amine (41) | 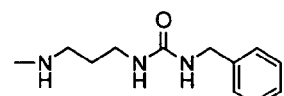 |
| Yoh. pyrrolidine-2,5-dione alkyl amine (42) | 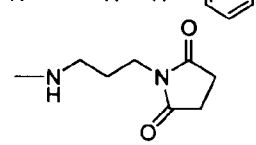 |
| Yoh. pyrrolidin-1-yl alkyl amine (43) | 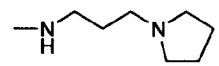 |
| Yoh. 1H-pyrrol-1-yl alkyl amine (44) | 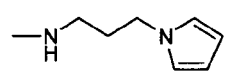 |
| Yoh. benzylimidazolidin-2-one alkyl amine (45) | 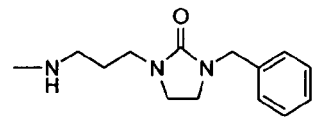 |
| Yoh. 1-benzylimidazolidine-2,4-dione alkyl amine (46) | 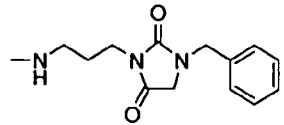 |
| Yoh. 3-benzylimidazolidine-2,4-dione alkyl amine (47) | 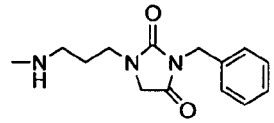 |
| Yoh. diglycine benzyl ester (48) | 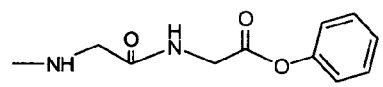 |
| Yoh. (benzyloxy)ethylacetamide amine (49) | 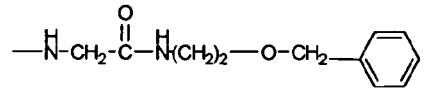 |
| Yoh. benzyl diacetamide amine (50) | 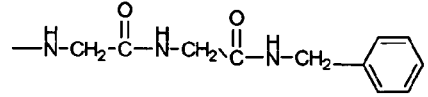 |
Figure 3B

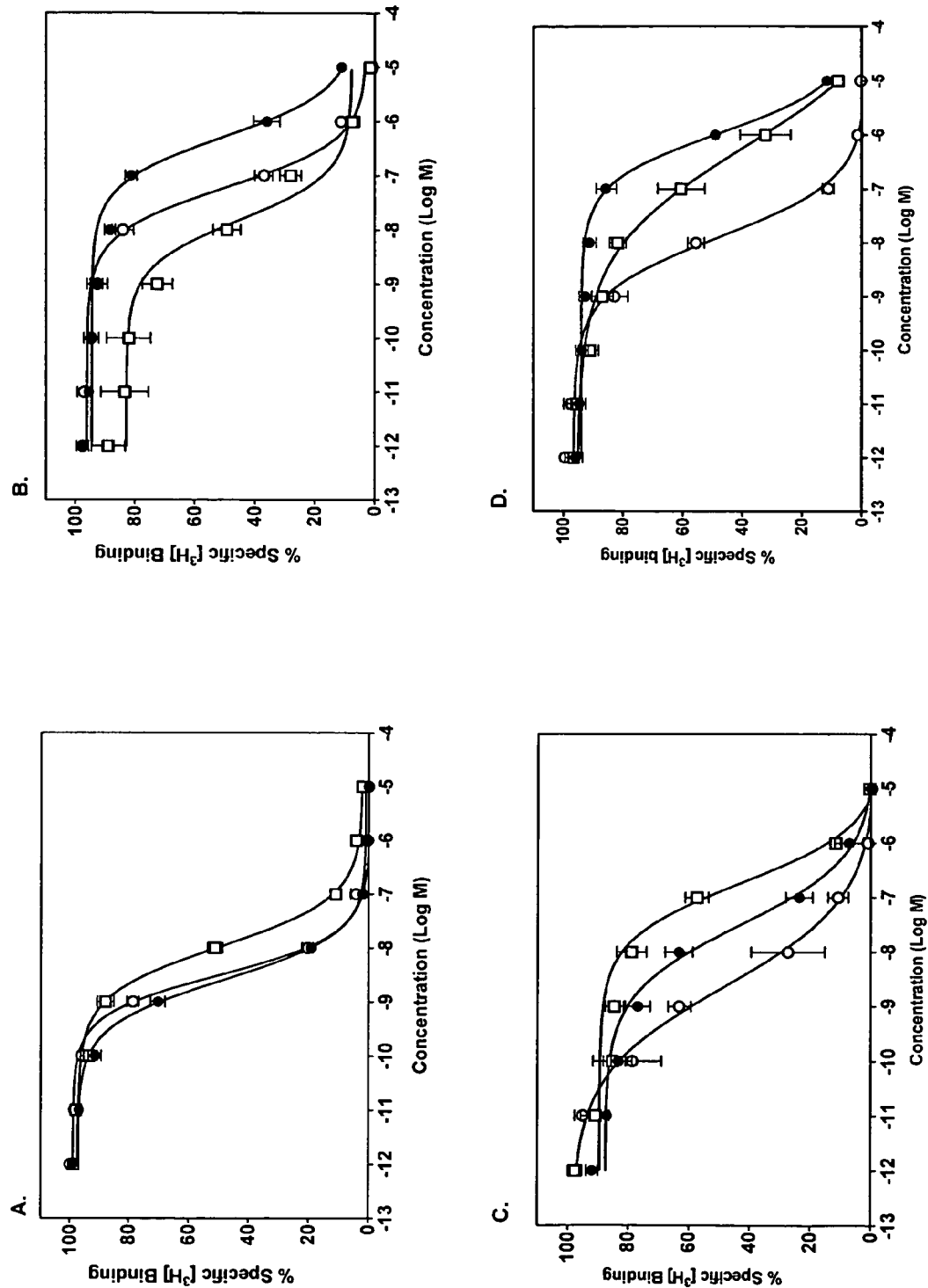
Figures 4A-D

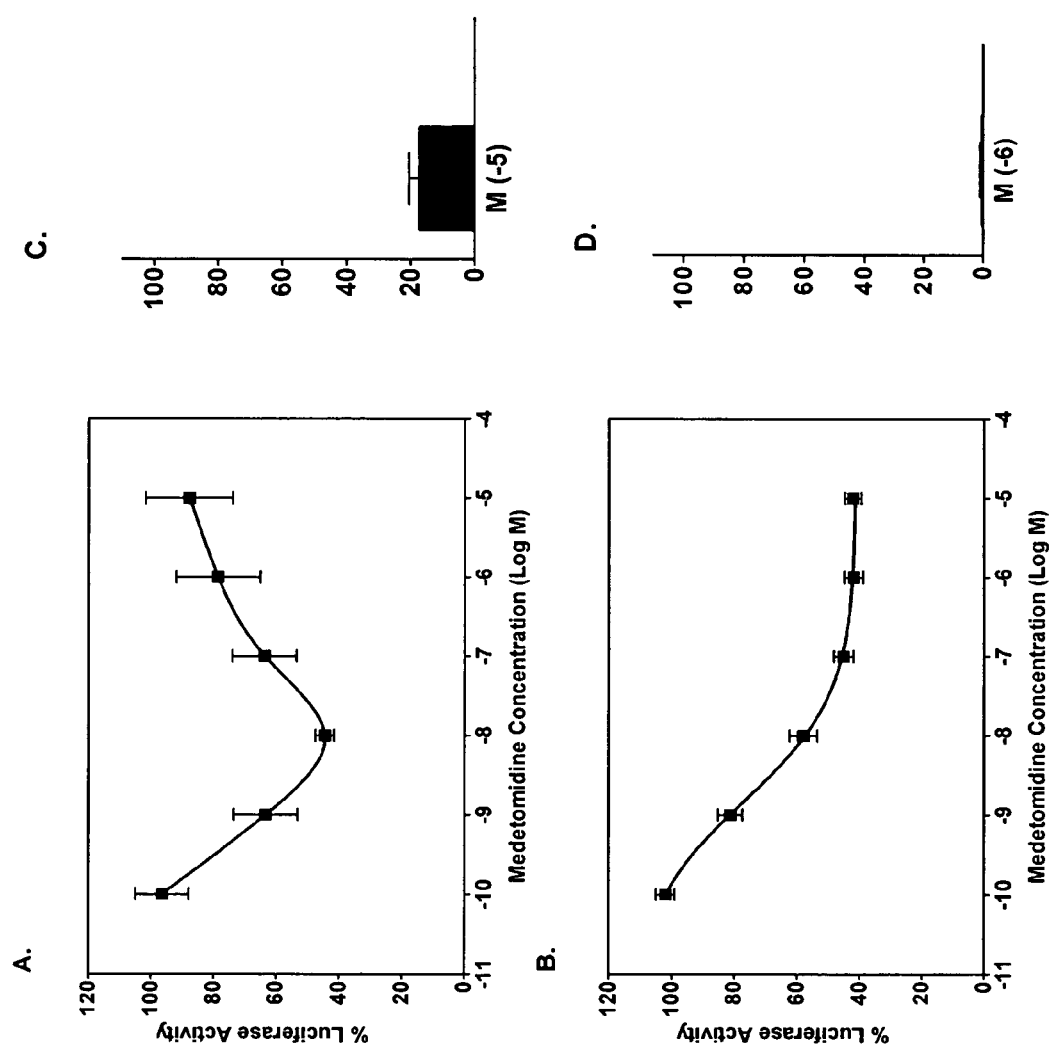
Figures 5A-D

Scheme 3. Reagents and Conditions: (a) benzyl chloroformate, NaOH, chloroform; (b) (Ph)$_3$P, Et$_2$O/EtOAc-5% HCl; (c) succinic anhydride, THF; (d) B$_2$H$_6$, THF (e) Pd/C, ethanol; (f) benzylisocyanate.

Scheme 4. Reagents and Conditions: (a) diethoxymethoxy-ethane; (b) BuLi; (c) H₂O; (d) NaH, THF; (e) Br(CH₂)₃-N(SiMe₃)₂, Et₂O; (f) H+, H₂O.

Scheme 5. Reagents and Conditions: (a) NaH, THF; (b) Br(CH₂)₃-N(SiMe₃)₂, Et₂O; (c) H+, H₂O.

Scheme 6. Reagents and Conditions: (a) DCC, HOBT; (b) (O)-benzyl-glycine; (c) H₂ Pd/C; (d) NH₃; (e) benzylbromide; (f) LAH, THF.

YOHIMBINE DERIVATIVES AND USE THEREOF

This application claims the priority benefit of U.S. Provisional Patent Application Ser. No. 60/603,584 filed Aug. 23, 2004, which is hereby incorporated by reference in its entirety.

The present invention was made with funding received from the National Institutes of Health under grant USPHS GM 29358, and from the United States Department of Agriculture under Cooperative Agreement No. 58-6408-2-0009. The U.S. government may retain certain rights in this invention.

FIELD OF THE INVENTION

The present invention relates to novel yohimbine derivatives and their use in modulating adrenergic receptor activity and in treating diseases or conditions mediated by such receptors.

BACKGROUND OF THE INVENTION

Adrenoreceptors (ARs) are membrane proteins belonging to the superfamily of G-protein-coupled receptors (Hoffman et al., "Radioligand Binding Studies of Adrenergic Receptors: New Insights into Molecular and Physiological Regulation," *Annu. Rev. Pharmacol. Toxicol* 20:581-608 (1980); Gerhardt et al., "Multiple $G_i$ Protein Subtypes Regulate a Single Effector Mechanism," *Mol. Pharmacol.* 40:707-711 (1991); Eason et al., "Simultaneous Coupling of α2-Adrenergic Receptors to Two G-proteins with Opposing Effects: Subtype-selective Coupling of $\alpha_{2C}10$, $\alpha_{2C}4$, and $\alpha_{2C}2$ Adrenergic Receptors to $G_i$ and $G_s$," *J. Biol. Chem.* 267:15795-15801 (1992)). With the aid of pharmacological and molecular biological techniques, the α-adrenoreceptor subtypes $\alpha_1$ and $\alpha_2$ were determined. Detailed studies have since shown that these initial subtypes are further divided into $\alpha_{1A}$, $\alpha_{1B}$, $\alpha_{1D}$, $\alpha_{2A}$, $\alpha_{2B}$, $\alpha_{2C}$, and $\alpha_{2D}$ subtypes, depending on species and tissues (Bylund, "Subtypes of α1- and α2-Adrenergic Receptors," *FASEB J.* 6:832-839 (1992); Bylund et al., "International Union of Pharmacology Nomenclature of Adrenoceptors," *Pharmacol. Rev.* 46:121-146 (1994); Hieble et al., "α- and β-Adrenoceptors: From the Gene to the Clinic. 1. Molecular Biology and Adrenoceptor Subclassification," *J. Med. Chem.* 38:3415-3444 (1995); Hieble et al., "Subclassification and Nomenclature of $\alpha_1$ and $\alpha_2$-Adrenoceptors," *Prog. Drug Res.* 47:81-130 (1996); Hieble, et al., "Functional Subclassification of $\alpha_2$-Adrenoceptors," *Pharmacol. Commun.* 6:91-97 (1995)).

This knowledge has led to a search for selective agonists and antagonists for each subtype. Although there are a number of $\alpha_2$-AR antagonists (Ruffolo et al., "α- and β-Adrenoceptors: From the Gene to the Clinic. 2. Structure-Activity Relationships and Therapeutic Applications," *J. Med. Chem.* 38, 3681-3716 (1995); Clark et al., "Pharmacology and Structure-Activity Relationships of $\alpha_2$-Adrenoceptor Antagonists," *Prog. Med. Chem.* 23:1-39 (1986)), only a small set of compounds have shown even a degree of selectivity among the three subtypes of $\alpha_2$-AR. However, these compounds suffer from either low subtype selectivity or binding to receptor sites outside the $\alpha_2$-AR subfamily (Ruffolo et al., "α- and β-Adrenoceptors: From the Gene to the Clinic. 2. Structure-Activity Relationships and Therapeutic Applications," *J. Med. Chem.* 38, 3681-3716 (1995); Okumura et al., "The Selectivity of Newly Synthesized Ergot Derivatives to $\alpha_1$- and $\alpha_2$-Adrenoceptors, $D_1$- and $D_2$-Dopaminergic Receptors, Muscarinic Acetylcholinoceptors and β-Adrenoceptors," *Gen. Pharmacol.* 19:463-466 (1988); Beeley et al., "Synthesis of a Selective $\alpha_{2A}$ Adrenoceptor Antagonist, BRL 48962, and its Characterization at Cloned Human α-Adrenoceptors," *Bioorg. Med. Chem.* 3:1693-1698 (1995); Blaxall et al., "Characterization of the $\alpha_{2C}$ Adrenergic Receptor Subtype in the Opossum Kidney and in the OK Cell Line," *J. Pharmacol. Exp. Ther.* 259:323-329 (1991); Bylund et al., "Pharmacological Characteristics of $\alpha_2$-Adrenergic Receptors: Comparison of Pharmacologically Defined Subtypes with Subtypes Identified by Molecular Cloning," *Mol. Pharmacol.* 42:1-5 (1992)).

Efforts made towards understanding the biological significance of each of the $\alpha_2$-adrenergic receptor subtypes (Bylund et al., Adrenoceptors, in *The IUPHAR Compendium of Receptor Characterization and Classification*, $1^{st}$ ed (1998), pp 58-74, IUPHAR Media Company, Burlington Press, Cambridge, England) have resulted only in marginal success due to the lack of subtype-selective ligands. The significance of functional groups in imidazoline compounds affecting selectivity and affinity in the $\alpha_2$-AR system were detailed recently by Pigini et al. (Pigini et al., "Imidazoline Receptors: Qualitative Structure-Activity Relationships and Discovery of Tracizoline and Benazoline, Two Ligands with High Affinity and Unprecedented Selectivity," *Bioorg. Med. Chem.* 5:833-841 (1997); Pigini et al., "Structure-Activity Relationship at α-Adrenergic Receptors Within a Series of Imidazoline Analogues of Cirazoline," *Bioorg. Med. Chem.* 8:883-888 (2000); Gentili et al., "$\alpha_2$-Adrenoreceptors Profile Modulation and High Antinociceptive Activity of (S)-(−)-2-[1-(biphenyl-2-yloxy)ethyl]-4,5-dihdryo-1H-Imidazole," *J. Med. Chem.* 45:32-40 (2002); Gentili et al., "Imidazoline Binding Sites (IBS) Profile Modulation: Key Role of the Bridge in Determining I1-IBS or I2-IBS Selectivity Within a Series of 2-Phenoxymethylimidazoline Analogues," *J. Med. Chem.* 46:2169-2176 (2003); Gentili et al., "$\alpha_2$-Adrenoreceptors Profile Modulation. 2. Biphenyline Analogues as Tools for Selective Activation of the $\alpha_{2C}$-subtype," *J. Med. Chem.* 47:6160-6173 (2004)).

This endeavor has been greatly assisted by genetic manipulation using mice with deletions, mutations, or overexpression of specific $\alpha_2$-AR subtypes. The role of the $\alpha_{2C}$-, in addition to the $\alpha_{2A}$-AR, in the feedback control of neurotransmitter release is a finding from one such study (Hein et al., "Two Functionally Distinct $\alpha_2$-Adrenergic Receptors Regulate Sympathetic Transmission," *Nature* 402:181-184 (1999)). Contribution of the $\alpha_{2C}$-ARs to $\alpha_2$-AR opioid synergy induced by certain agonists such as moxonidine is another finding (Fairbanks et al., "$\alpha_{2C}$-Adrenergic Receptors Mediate Spinal Analgesia and Adrenergic-Opioid Synergy," *J. Pharmacol. Exp. Ther.* 300:282-290 (2002)). Together, these findings suggest that the $\alpha_{2C}$-AR may represent a better therapeutic target for analgesic therapy than the $\alpha_{2A}$-AR, since this subtype would also lead to fewer sedative effects.

In the central nervous system, the $\alpha_{2C}$-ARs appear to have a distinct inhibitory role in various CNS-mediated behavioral and physiological responses including startle reactivity, aggressive behavior, and amphetamine-induced locomotor hyperactivity (Scheinin et al., "Evaluation of the $\alpha_{2C}$-adrenoceptor as a Neuopsychiatric Drug Target: Studies in Transgenic Mouse Models," *Life Sci.* 68:2277-2285 (2001)). Increased $\alpha_{2C}$-AR activity may lead to, or result from, a constitutively stressful state thereby causing depression. $\alpha_{2C}$-AR subtype-selective drugs, therefore, may be useful in a variety of neuropsychiatric disorders (Scheinin et al., "Evaluation of the $\alpha_{2C}$-adrenoceptor as a Neuopsychiatric Drug Target: Studies in Transgenic Mouse Models," *Life Sci.* 68:2277-2285 (2001)).

Beside these findings derived from gene-targeted mice, a recent study (Chotani et al., "Silent $\alpha_{2C}$-adrenergic Receptors Enable Cold-induced Vasoconstriction in Cutaneous Arteries," *Am. J. Physiol. Heart Circ. Physiol.* 278:1075-1083 (2000)) has identified yet another therapeutic use for an $\alpha_{2C}$-AR antagonist. The study showed that at lower temperatures the $\alpha_{2C}$-ARs are principally responsible for mediating the cold-induced augmented vasoconstrictor response. This subtype, however, did not contribute to $\alpha_2$-AR dependent vasoconstriction at 37° C. A selective inhibition of the $\alpha_{2C}$-ARs in microvessels has, thus, been proposed to provide an effective treatment for cold-induced cutaneous arterial blood vessel constriction as observed in Raynaud's phenomenon. The importance of $\alpha_{2C}$-AR antagonists in treating Raynaud's disease was illustrated by Flavahan et al. (U.S. Pat. No. 6,444,681 to Flavahan et al.; Chem. Abstr. 137:103 (2002)). The most common probes used in these studies are agonists such as clonidine, and antagonists such as yohimbine and yohimbine like compounds viz. rauwolscine, corynanthine.

FIG. 1 illustrates the structure of several prior art compounds, including yohimbine 1, which is known to be a potent $\alpha_2$-AR antagonist, and has been used extensively as a pharmacological probe for studying the $\alpha_2$-AR (Goldberg et al., "Yohimbine: A Pharmacological Probe for Study of the $\alpha_2$-Adrenoreceptor," *Pharmacol. Rev.* 35:143-180 (1983)). To improve subtype selectivity, the bivalent ligand approach was introduced recently based on the concept that a bivalent ligand should first undergo univalent binding, followed by the binding of the second pharmacophore to a recognition site on a neighboring receptor (Portoghese, Portoghese, 2000 Alfred Burger Award Address in Medicinal Chemistry, "From Models to Molecules: Opioid Receptor Dimers, Bivalent Ligands, and Selective Opioid Receptor Probes," *J. Med. Chem.* 44:2259-2269 (2001)). Using this approach, several yohimbine dimers were prepared with methylene and methylene-diglycine spacer linkages. It was discovered that such compounds with spacers of n=3(2) and n=24(3) showed the highest potency and selectivity for the $\alpha_{2C}$-AR in receptor binding studies and in functional studies measuring cAMP changes using a cell-based luciferase reporter gene assay (Zheng et al., "Yohimbine Dimers Exhibiting Binding Selectivities for Human $\alpha_{2a}$- Versus $\alpha_{2b}$-Adrenergic Receptors," *Bioorg. Med. Chem. Lett.* 10:627-630 (2000); Lalchandani et al., "Yohimbine Dimers Exhibiting Selectivity for the Human $\alpha_{2C}$-AR Subtype," *J. Pharmacol. Exp. Ther.* 303, 979 (2002); U.S. Pat. No. 6,638,943 to Miller et al.; Chem. Abstr. 137:794 (2002)). Interestingly, none of the dimer analogs surpassed the affinity of yohimbine.

Despite the prior advances concerning pharmaceutical selectivity of $\alpha_2$-adrenoceptor subtypes, it would be desirable to identify other compounds with selectivity for particular of $\alpha_2$-adrenoceptor subtype such as the $\alpha_{2C}$-AR, and preferably compounds that exhibit both high affinity and receptor subtype selectivity.

The present invention is directed to overcoming these and other deficiencies in the art.

SUMMARY OF THE INVENTION

A first aspect of the present invention relates to a yohimbine derivative having a C-16 sidechain (i.e., replacing the C-16 methoxy group of yohimbine) with one or more neutral, basic, or acidic functional group(s), and wherein the yohimbine derivative is selective antagonist of the $\alpha_{2C}$-adrenoreceptor.

Preferred yohimbine derivatives of the present invention have the structure according to formula (I) as follows:

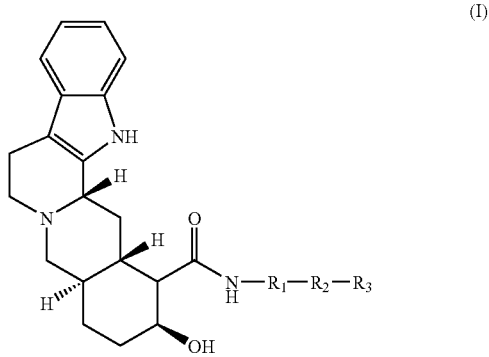

(I)

wherein,

R$_1$ is either an aliphatic C$_{1-20}$ hydrocarbon, or an aromatic or heteroaromatic ring that is monocyclic or polycyclic;

R$_2$ is optional and is selected from the group of —N(H)— and carbonyl-containing linking groups;

R$_3$ is selected from the group of H, COOH, NH$_2$, an aliphatic C$_{1-30}$ hydrocarbon, an aromatic or hetero-aromatic ring that is monocylic or polycyclic, and hydrocarbon-R$_4$ where the hydrocarbon is an aliphatic C$_{1-30}$ hydrocarbon;

R$_4$ is selected from the group of COOH, NH$_2$, C$_{5-7}$ cycloalkyl, an aromatic or hetero-aromatic ring that is monocyclic or polycyclic, or

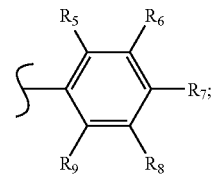

and

R$_5$, R$_6$, R$_7$, R$_8$, and R$_9$ are independently selected from the group of H, OH, C$_{1-6}$ alkyl, halo, amino, C$_{1-2}$ alkylamino, C$_{1-2}$ dialkylamino, amido, C$_{1-2}$ alkylamido, cyano, nitro, C$_{1-6}$ alkoxy, C$_{1-6}$ alcohol, carboxyl containing a C$_{1-6}$ alkyl, carbonyl containing a C$_{1-6}$ alkyl, and an ester containing a C$_{1-6}$ alkyl group.

A second aspect of the present invention relates to a pharmaceutical composition that includes a compound according to the first aspect of the present invention and a pharmaceutically acceptable carrier.

A third aspect of the present invention relates to a method of treating or preventing an $\alpha_{2c}$ adrenergic receptor mediated condition or disorder that includes: administering to a patient an effective amount of a compound according to the first aspect of the present invention under conditions effective to treat or prevent the $\alpha_{2c}$ adrenergic receptor mediated condition or disorder.

A fourth aspect of the present invention relates to a method of antagonizing activity of an $\alpha_{2c}$ adrenergic receptor that includes: contacting an $\alpha_{2c}$ adrenergic receptor with a compound according to the first aspect of the present invention under conditions effective to antagonize the activity of the $\alpha_{2c}$ adrenergic receptor, wherein the compound selectively antagonizes the $\alpha_{2c}$ adrenergic receptor over other adrenergic receptors.

The compounds of the present invention show great promise in providing a therapeutic agent that can selectively treat $\alpha_{2c}$-AR mediated diseases or conditions, particularly Raynaud's Disease, peripheral $\alpha_{2c}$-AR vasoconstriction possibly associated with hypertension, and various CNS disorders such as depression, anxiety, and forms of attention deficit disorder. Compounds of the present invention have shown activity comparable to that of yohimbine, but with selectivities over the several $\alpha_1$-AR and both the $\alpha_{2a}$-AR and $\alpha_{2b}$-AR. Selectivities greater than 100-fold have been demonstrated. As a consequence, the compounds of the present invention should afford a treatment at sufficient doses where unintended side-effects, manifested through the other AR, can be limited or avoided altogether.

BRIEF DESCRIPTION OF THE DRAWINGS

FIG. 1 is illustrates the structure of yohimbine and several prior art yohimbine dimers.

FIG. 2A illustrates several synthesis schemes for preparing yohimbine derivatives of the present invention. FIG. 2B illustrates a synthesis scheme for preparing intermediate amines used for synthesizing yohimbine derivatives of the present invention.

FIGS. 3A-B illustrate the chemical structures of yohimbine and several yohimbine derivatives of the present invention, particularly the side chains thereof.

FIGS. 4A-D are graphs of binding displacement curves for yohimbine (4A), yohimbinic acid (4B), yohimbine benzyl carboxy alkyl amine (4C), and yohimbine carboxy alkyl amine (4D) for human $\alpha_{2A}$-, $\alpha_{2B}$-, and $\alpha_{2C}$-ARs stably expressed in CHO cells. Plotted values are the mean±SEM (n=4-6 experiments). Structures of compounds are shown in FIGS. 1 and 3. Key: •, $\alpha_{2A}$; □, $\alpha_{2B}$; and ○, $\alpha_{2C}$.

FIGS. 5A-D illustrate concentration-dependent effects of medetomidine on forskolin-induced cAMP elevations, as assessed by luciferase activity, on human $\alpha_{2A}$-ARs (5A) versus $\alpha_{2C}$-ARs (5B) stably expressed in CHO cells. FIGS. 5C-D illustrate the effect of a high concentration of medetomidine alone (in the absence of forskolin) on human $\alpha_{2A}$- and $\alpha_{2C}$-ARs, respectively. Plotted values are the mean±SEM (n=4 or more experiments). Key: M, medetomidine.

DETAILED DESCRIPTION OF THE INVENTION

Figure 6:
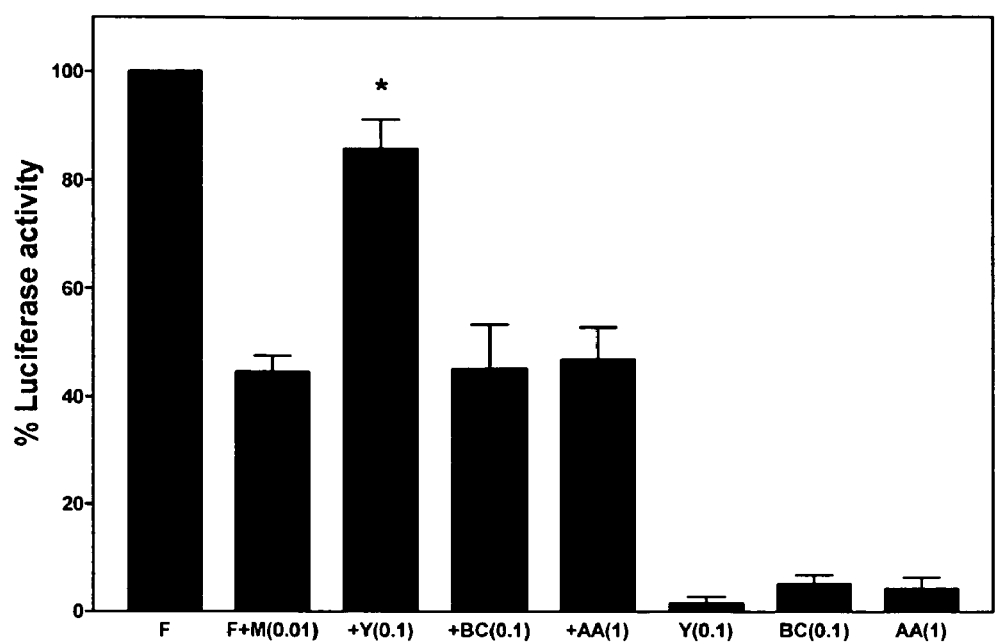
FIG. 6 illustrates the effects of yohimbine and selected tethered monomeric yohimbine derivatives on medetomidine inhibition of forskolin-induced cAMP elevations, as assessed by luciferase activity, on human $\alpha_{2A}$-ARs stably expressed in CHO cells. Plotted values are the mean±SEM (n=5 experiments). Structures of compounds are shown in FIGS. 1 and 3. Key: F, forskolin (5 µM); M, medetomidine (0.01 µM); Y, yohimbine (0.1 µM); BC, yohimbine benzyl carbamate alkyl amine monomer (0.1 µM); and AA, yohimbine alkyl amine monomer (1 µM). * Indicates P<0.05 compared to F+M(1) using Student's t test.

The present invention relates to derivatives of yohimbine that have a modification of the C-16 carboxyl group to include a sidechain (i.e., other than the methoxy of yohimbine) and where the resulting derivative does not possess a second yohimbine pharmacophore (i.e., the compound is not a yohimbine dimer). The yohimbine derivatives of the present invention are preferably characterized by selective activity as $\alpha_{2C}$-AR antagonists. The sidechain is preferably one containing either neutral, basic, or acidic functional group(s).

Preferred C-16 derivatized yohimbine molecules of the present invention have the structure according to formula (I) below:

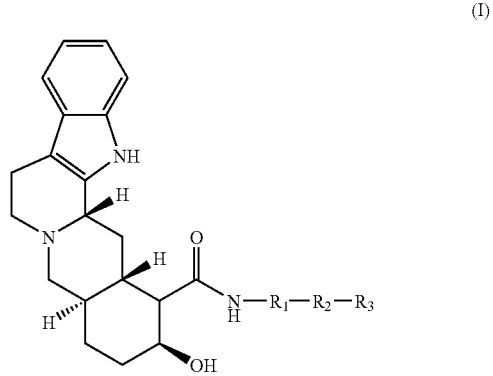

(I)

wherein,
$R_1$ is either a $C_{1-20}$ hydrocarbon, or an aromatic or heteroaromatic ring that is monocyclic or polycyclic;
$R_2$ is optional and is selected from the group of —N(H)— and carbonyl-containing linking groups including, without limitation, —C(O)—O—, —N(H)—C(O)—O—, —C(O)—, —N(H)—C(O)—, —N(H)—C(O)—N(H)—,

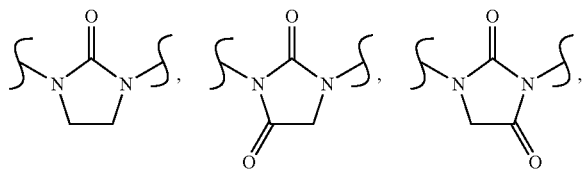

—C(O)—N(H)—C$_{2-10}$ hydrocarbon-O—, —C(O)—N(H)—C$_{2-10}$ hydrocarbon-C(O)—N(H)—, or —C(O)—N(H)—C$_{2-10}$ hydrocarbon-C(O)—O—;

R$_3$ is selected from the group of —H, —COOH, —NH$_2$, a C$_{1-30}$ hydrocarbon, an aromatic or hetero-aromatic ring that is monocylic or polycyclic, and hydrocarbon-R$_4$ where the hydrocarbon is a C$_{1-30}$ hydrocarbon;

R$_4$ is selected from the group of —COOH, —NH$_2$, C$_{5-7}$ cycloalkyl, an aromatic or hetero-aromatic ring that is monocyclic or polycyclic, or

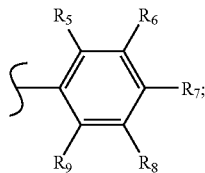

and

R$_5$, R$_6$, R$_7$, R$_8$, and R$_9$ are independently selected from the group of —H, —OH, C$_{1-6}$ alkyl, halo, amino, C$_{1-2}$ alkylamino, C$_{1-2}$ dialkylamino, amido, C$_{1-2}$ alkylamido, cyano, nitro, C$_{1-6}$ alkoxy, C$_{1-6}$ alcohol, carboxyl containing a C$_{1-6}$ alkyl, carbonyl containing a C$_{1-6}$ alkyl, and an ester containing a C$_{1-6}$ alkyl group.

As identified above, the various hydrocarbon groups can be saturated or unsaturated, or polyunsaturated aliphatic hydrocarbons, and with or without branches. Preferred aliphatic hydrocarbon groups are saturated. Branched-chain hydrocarbons preferably contain branches that are less than about 3 carbons in length.

As identified above, the various aromatic or hereto-aromatic monocylic and polycyclic ring(s) independently can be aromatics (e.g., phenyl, biphenyl, napthyl, anthracenyl), N-hetero aromatics (e.g., pyrrolyl, indolyl, isoindolyl, imidazolyl, benzimidazolyl, purinyl, pyrazolyl, indazolyl, pyridinyl, quinolinyl, isoquinolinyl, pyrazinyl, quinoxalenyl, pyrimidinyl, cinnolinyl, quinazolinyl, pyrrolidinyl), S-hetero aromatics (e.g., thiophenyl, benzthiophenyl), O-hetero aromatics (e.g., furanyl, benzofuranyl, isobenzofuranyl), and mixed hetero aromatics (e.g., thiazolyl, benzthiazolyl, oxazolyl, benzoxazolyl, isooxazolyl, benisooxazolyl).

Preferred R$_1$ groups include, without limitation, C$_{2-18}$ hydrocarbons, more preferably C$_{3-15}$ hydrocarbons; the R$_1$ hydrocarbons are preferably saturated.

Preferred R$_2$ groups are carbonyl-containing linking groups, more preferably —C(O)—O—, —N(H)—C(O)—O—, —C(O)—, —N(H)—C(O)—, or —N(H)—C(O)—N(H)—.

Preferred R$_3$ groups include, without limitation, —COOH, a C$_{3-30}$ hydrocarbon that is saturated, and hydrocarbon-R$_4$ where R$_4$ is —COOH or a substituted or unsubstituted phenyl ring.

Exemplary compounds of the present invention are illustrated in FIGS. 3A-3B and include, without limitation, yohimbine monoglycine ester, yohimbine diglycine ester, yohimbine t-butyl carbamate alkyl amine, yohimbine benzyl carbamate alkyl amine, yohimbine alkyl amine, yohimbine benzyl carboxy alkyl amine, yohimbine carboxy alkyl amine, yohimbine benzylurea alkyl amine, yohimbine pyrrolidine-2,5-dione alkyl amine, yohimbine pyrrolidin-1-yl alkyl amine, yohimbine 1H-pyrrol-1-yl alkyl amine, yohimbine benzylimidazolidin-2-one alkyl amine, yohimbine 1-benzylimidazolidine-2,4-dione alkyl amine, yohimbine 3-benzylimidazolidine-2,4-dione alkyl amine, yohimbine diglycine benzyl ester, yohimbine (benzyloxy)ethylacetamide amine, and yohimbine benzyl diacetamide amine. Of these, yohimbine t-butyl carbamate alkyl amine, yohimbine benzyl carbamate alkyl amine, yohimbine benzyl carboxy alkyl amine, and yohimbine carboxy alkyl amine are more preferred, with yohimbine t-butyl carbamate propyl amine (8), yohimbine benzyl carbamate propyl amine (7), yohimbine benzyl carboxy propyl amine (10), and yohimbine carboxy propyl amine (11) being most preferred.

Preferred compounds of the present invention are active at the $\alpha_{2c}$-AR and are characterized by selectivity for the $\alpha_{2c}$-AR over either the $\alpha_{2a}$-AR, the $\alpha_{2b}$-AR, or more preferably both the $\alpha_{2a}$-AR and the $\alpha_{2b}$-AR. As used herein, selectivity is intended to mean that a compound has a higher pK$_i$ value for the $\alpha_{2c}$-AR as compared to the corresponding pK$_i$ values at one or both of the $\alpha_{2a}$-AR and the $\alpha_{2b}$-AR. Preferably, the compounds have at least about 10-fold selectivity over one or both of the $\alpha_{2a}$-AR and $\alpha_{2b}$-AR, more preferably at least about 25-fold selectivity over one or both of the $\alpha_{2a}$-AR and $\alpha_{2b}$-AR, most preferably at least about 50-fold selectivity over one or both of the $\alpha_{2a}$-AR and $\alpha_{2b}$-AR. Even higher selectivity has been obtained (see Examples and Discussion, infra), and is preferred.

The compounds of the present invention can be prepared by reacting yohimbine and a desired amine starting material (e.g., NH$_2$—R$_1$—R$_2$—R$_3$) under standard peptide coupling conditions. In particular, 1,3-Dicyclohexylcarbodiimide (DCC) has been used as the coupling agent and N-hydroxybenzotriazole (HOBT) has been used as an additive to catalyze the reaction and to suppress epimerization at the C-16 position of yohimbine. The desired amine starting material can either be purchased directly or synthesized as desired, for example as shown in FIGS. 2A-B and 9A-D.

The compounds prepared by the methods of the present invention can in some circumstances be in the form of pharmaceutically acceptable salts, i.e., inorganic or organic acid or base addition salts of the above compounds. Suitable inorganic acids are, for example, hydrochloric, hydrobromic, sulfuric, and phosphoric acids. Suitable organic acids include carboxylic acids, such as, acetic, propionic, glycolic, lactic, pyruvic, malonic, succinic, fumaric, malic, tartaric, citric, cyclamic, ascorbic, maleic, hydroxymaleic, dihydroxymaleic, benzoic, phenylacetic, 4-aminobenzoic, anthranilic, cinnamic, salicylic, 4-aminosalicylic, 2-phenoxybenzoic, 2-acetoxybenzoic, and mandelic acid. Sulfonic acids, such as, methanesulfonic, ethanesulfonic, and α-hydroxyethane-sulfonic acid are also suitable acids. Non-toxic salts of the compounds of the above-identified formulae formed with inorganic and organic bases include, for example, those alkali metals, such as, sodium, potassium, and lithium, alkaline earth metals, for example, calcium and magnesium, light metals of group IIIA, for example, aluminum, organic amines, such as, primary, secondary, or tertiary amines, for example, cyclohexylamine, ethylamine, pyridine, methylaminoethanol, and piperazine.

Another aspect of the present invention relates to a pharmaceutical composition, which includes a yohimbine derivative (including salts thereof) as described above and a pharmaceutically acceptable adjuvant, carrier, and/or excipient.

The compounds or compositions prepared according to the present invention can be used to treat warm blooded animals that possess $\alpha_{2c}$-AR, such as mammals. Examples of suitable mammals include, without limitation, humans, cats, dogs, horses, sheep, cows, pigs, rats, mice, and guinea pigs.

Conventional administration methods may be suitable for use in the present invention as described below.

Compounds or compositions within the scope of this invention include all compounds or compositions, wherein the compound of the present invention is contained in an amount effective to achieve its intended purpose. While individual needs vary, determination of optimal ranges of effective amounts of each component is within the skill of the art. The quantity of the compound or composition administered will vary depending on the patient and the mode of administration and can be any effective amount. Typical dosages include about 0.01 to about 100 mg/kg.body wt. The preferred dosages include about 0.01 to about 0.1 mg/kg.body wt up to three times a day. Treatment regimen for the administration of the compounds of the present invention can also be determined readily by those with ordinary skill in art. The quantity of the compound administered may vary over a wide range to provide in a unit dosage an effective amount of from about 0.01 to 20 mg/kg of body weight of the patient per day to achieve the desired effect.

The compounds of the present invention can be utilized as the biologically active components in pharmaceutical compositions. The pharmaceutical composition can also include, but are not limited to, suitable adjuvants, carriers, excipients, or stabilizers, and can be in solid or liquid form such as, tablets, capsules, powders, solutions, suspensions, or emulsions. Typically, the composition will contain from about 0.01 to 99 percent, preferably from about 20 to 75 percent of active compound(s), together with the adjuvants, carriers and/or excipients.

Depending upon the treatment being effected, the compounds or compositions of the present invention can be administered orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

The solid unit dosage forms can be of the conventional type. The solid form can be a capsule and the like, such as an ordinary gelatin type containing the compounds of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, these active compounds can be incorporated with excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 mg and 800 mg of active compound.

The active compounds of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions of the present invention may also be administered in injectable dosages by solution or suspension of these materials in a physiologically acceptable diluent with a pharmaceutical adjuvant, carrier or excipients. Such adjuvants, carriers and/or excipients, include, but are not limited to sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

The active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the active compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The present invention also relates to the use of the compounds or compositions of the present invention for modulating the activity of an $\alpha_2$-AR, preferably selectively antagonizing the activity of $\alpha_{2c}$-AR versus one or both of the $\alpha_{2a}$-AR and $\alpha_{2b}$-AR. This aspect of the present invention can be achieved by contacting an $\alpha_{2c}$ adrenergic receptor with a yohimbine derivative of the present invention under conditions effective to antagonize the activity of the $\alpha_{2c}$ adrenergic receptor (i.e., without substantially modifying the activity of one or both of the $\alpha_{2a}$-AR and $\alpha_{2b}$-AR). While some antagonism of the $\alpha_{2a}$-AR and/or $\alpha_{2b}$-AR can occur, the extent of such antagonism can be minimized by control of dosage (while maintaining effective antagonism of the $\alpha_{2c}$-AR). Preferably, the degree of $\alpha_{2a}$-AR and/or $\alpha_{2b}$-AR antagonism is insubstantial to the extent that any side effects are mild or non-existent.

According to this aspect of the present invention, the $\alpha_{2c}$-AR to be antagonized is present on a cell. The cell can be located either ex vivo or in vivo.

In so modulating the activity of an $\alpha_{2c}$ adrenergic receptor, it is possible to treat or prevent an $\alpha_{2c}$ adrenergic receptor mediated condition or disorder of the type listed below. This can be achieved by administering to a patient an effective amount of a yohimbine derivative of the present invention under conditions effective to selectively antagonize the $\alpha_{2c}$ adrenergic receptor, and thereby treat or prevent the $\alpha_{2c}$ adrenergic receptor mediated condition or disorder. More specifically, to treat or prevent disorders or conditions that involve the activity of normally silent $\alpha_{2c}$-AR, this receptor subtype can be selectively targeted relative to the $\alpha_{2a}$-AR and $\alpha_{2b}$-AR. As a result, numerous side-effects associated with either $\alpha_{2a}$-AR or $\alpha_{2b}$-AR antagonism can be avoided or at least minimized (vis-à-vis the effects of a non-selective antagonist such as yohimbine).

Suitable conditions for the modulation of the $\alpha_2$ adrenergic receptor relate to the fact that $\alpha_2$ receptors are located both pre-synaptically at nerve terminals and post-synaptically as in vascular smooth muscles, platelets, pancreatic β-cells, and fat cells. Activation of the presynaptic receptors inhibit the release of norepinephrine by a negative feedback mechanism, whereas blockade of these receptors would therefore increase the release of norepinephrine. The compounds of the present invention will also block the actions of catecholamines (norepinephrine and epinephrine) at post-synaptic receptors in target tissues. Thus, the compounds and compositions of the present invention will interact with both pre- and post-synaptic $\alpha_{2c}$-AR, and these dual actions may be regulated in treating disorders mediated by the $\alpha_{2c}$-AR.

Yohimbine is known to be an antagonist of $\alpha_{2c}$-AR. This invention is directed to yohimbine derivatives that are selective antagonists of human $\alpha_{2c}$ receptors, showing excellent selectivity between the $\alpha_{2c}$ receptors and the $\alpha_{2a}$ and $\alpha_{2b}$ receptors. Thus, the yohimbine derivatives of the present invention are particularly well suited for selectively inhibiting $\alpha_{2c}$-AR activity. As a result, the present invention also relates to the use of these compounds for treating or preventing disorders that implicate the activity of normally silenced $\alpha_{2c}$ adrenergic receptors. Exemplary disorders or conditions involving $\alpha_{2c}$-AR activity include, without limitation, Raynaud's Disease, and CNS disorders such as depression, anxiety, and attention deficit disorder (ADD).

The $\alpha_{2c}$ adrenergic receptors have been implicated in Raynaud's disease. The remarkable role of $\alpha_{2c}$-ARs in vascular dysfunction has only recently been discovered. Analysis of cutaneous arteries at 37° C. confirms that $\alpha_{2c}$-ARs do not normally contribute to vasoconstriction. However, Flavahan and coworkers (Chotani et al., "Silent α2c-Adrenergic Receptors Enable Cold-Induced Vasoconstriction in Cutaneous Arteries," *Heart and Circulatory Physiology*, 278:H1075-H1083 (2000); Flavahan et al., "Increased Alpha2-Adrenergic Constriction of Isolated Arterioles in Diffuse Sceleroderma," *Arthritis and Rheumatism*, 43:1886-1890 (2000), each of which is hereby incorporated by reference in its entirety) have shown that during cold-induced vasoconstriction (28° C.), the $\alpha_{2c}$-ARs are "no longer silent" and are proposed to be responsible for the vasospastic episodes in Raynaud's disease.

Recent studies in the mouse tail artery confirm the previous observations that the $\alpha_{2c}$-AR are activated at lower temperatures (Chotani et al., "Silent α2c-Adrenergic Receptors Enable Cold-Induced Vasoconstriction in Cutaneous Arteries," *Heart and Circulatory Physiology*, 278:H1075-H1083 (2000), which is hereby incorporated by reference in its entirety). At 37° C., the vasoconstriction is mediated by $\alpha_{2a}$- and/or $\alpha_{2b}$-ARs while $\alpha_{2c}$-ARs are not, or are only minimally, involved. However, in a remarkable way, the augmented vasoconstrictor response at 28° C. to catecholamines is mediated primarily by the $\alpha_{2c}$-AR. This work implies that $\alpha_{2c}$-ARs are "silent" at 37° C., but are activated during cold-induced exposures, e.g. at 28° C.

The Flavahan group reported that cold induced vasoconstriction is related to an increased distribution of $\alpha_{2c}$-ARs from the Golgi apparatus to the cellular membranes (Jeyaraj et al., "Cooling Evokes Redistribution of Alpha2C-Adrenoceptors from Golgi to Plasma Membrane in Transfected Human Embryonic Kidney 293 Cells," *Mol. Pharmacol.*, 60:1195-200 (2001), which is hereby incorporated by reference in its entirety). The mechanism that silences or suppresses the actions of the $\alpha_{2c}$-ARs at 37° C. is unknown. The specific temperature effect on the $\alpha_{2c}$-ARs could reflect altered membrane targeting or processing of the $\alpha_{2c}$-ARs or variations in the signaling or amplification process.

The "Raynaud's Disease Phenomenon" results from the vasospasms in the digital arterioles in response to cold, causing a sharp demarcated cutaneous pallor and cyanosis of the digits (Ekenvall et al., "Alpha-Adrenoceptors and Cold Induced Vasoconstriction in Human Finger Skin," *Am. J. Physiol.*, 255:H1000-H1003 (1988); Lewis et al., "Experiments Relating to the Peripheral Mechanism Involved in Spasmodic Arrest of the Circulation in Fingers: A Variety of Raynaud's Disease," *Heart*, 15:7-101 (1929), each of which is hereby incorporated by reference in its entirety). Studies with human patients show that vascular dysfunction is an important early defect in systemic sclerosis (scleroderma) which occurs prior to tissue fibrosis (Flavahan et al., "Increased Alpha2-Adrenergic Constriction of Isolated Arterioles in Diffuse Scleroderma," *Arthritis and Rheumatism*, 43:1886-1890 (2000), which is hereby incorporated by reference in its entirety).

As used herein, the term treating is meant to include treatment that will substantially ameliorate the symptoms associated with a particular disease or condition, or at least minimize (i.e., reduce the severity) of such symptoms. Administration prior to onset of symptoms (i.e., in a presymptomatic patient) can be used to prevent development or delay onset of such symptoms.

Stable cell lines expressing the human $\alpha_2$ adrenergic receptors described above as well as stable cell lines expressing the human $\alpha_1$ adrenergic receptors have been deposited with the American Type Culture Collection (ATCC), 12301 Parklawn Drive, Rockville, Md., 20852, U.S.A., under the provisions of the Budapest Treaty for the International Recognition of the Deposit of Microorganisms for the Purposes of Patent Procedure. The cell line expressing the human $\alpha_{2a}$ receptor is designated L-$\alpha_{2a}$ and was deposited on Nov. 6, 1992, under ATCC Accession Number CRL-11180. The cell line expressing the human $\alpha_{2b'}$ receptor is designated L-NGC-$\alpha_{2b}$ and was deposited on Oct. 25, 1989 under ATCC Accession Number CRL-10275. The cell line expressing the human $\alpha_{2c}$ receptor is designated L-$\alpha_{2c}$ and was deposited on Nov. 6, 1992, under ATCC Accession Number CRL-11181.

EXAMPLES

The following examples are intended to illustrate the present invention but are by no means intended to limit the scope of the appended claims.

Materials and Methods

Sources of Materials

All cell culture reagents were obtained from Invitrogen (Carlsbad, Calif.). CHO cells expressing homogeneous populations of human $\alpha_{2A}$-, $\alpha_{2B}$- and $\alpha_{2C}$-ARs were obtained from Drs. Marc Caron, Dr. Robert Lefkowitz (Duke University Medical Center, Durham, N.C.) and Dr. Stephen Liggett (College of Medicine, University of Cincinnati, Cincinnati, Ohio). HEK293 cells expressing homogeneous populations of human $\alpha_{1A}$-, $\alpha_{1B}$- and $\alpha_{1D}$-ARs were obtained from Dr. Kenneth Minneman (Emory University School of Medicine, Atlanta, Ga.). The cAMP response element-luciferase gene construct (6 CRE-LUC) was provided by Dr. A. Himmler (Boehringer Ingelheim Research & Development, Vienna, Austria). Yohimbine (1) and yohimbinic acid (2) were obtained from ICN Biomedicals Inc. (Aurora, Ohio), and Aldrich Chemicals Co. (Milwaukee, Wis.), respectively. The n=3 and n=24 yohimbine dimers were synthesized according to the procedures described in U.S. Pat. No. 6,638,943 to Miller et al.; Zheng et al., "Yohimbine Dimers Exhibiting Binding Selectivities for Human $\alpha_{2a}$- versus $\alpha_{2b}$-Adrenergic Receptors," *Bioorg. Med. Chem. Lett.* 10:627-630 (2000), each of which is hereby incorporated by reference in its entirety. Solutions of the n=3 (3) and n=24 (4) yohimbine dimers (FIG. 1) were prepared as described previously (Lalchandani et al., "Yohimbine Dimers Exhibiting Selectivity for the Human $\alpha_{2C}$-AR Subtype," *J. Pharmacol. Exp. Ther.* 303:979-984 (2002), which is hereby incorporated by reference in its entirety).

Yohimbinic acid (2) and all the tethered monomeric yohimbine analogs, with the exception of the alkyl amine analog (9) and the carboxy alkyl amine analog (11), were dissolved in a mixture of water and dimethyl sulfoxide. Yohimbine (1), the alkyl amine analog (9) and the carboxy alkyl amine analog (11) were dissolved in water alone. Stock solutions ($10^{-2}$ M) were prepared and diluted in water to appropriate concentrations for the studies. [$^3$H]Rauwolscine and [$^3$H]prazosin were obtained from Perkin Elmer Life Sciences (Boston, Mass.) and all other chemicals were obtained from Sigma-Aldrich (St. Louis, Mo.).

Cell Culture

CHO cells stably expressing homogeneous populations of $\alpha_{2A}$-, $\alpha_{2B}$- and $\alpha_{2C}$-ARs were grown in 150 cm$^2$ Corning flasks with Ham's F-12 medium supplemented with 10% fetal bovine serum, 2 mM glutamine, penicillin (100 units/ml) and streptomycin (100 µg/ml). The flasks were incubated at 37° C. (5% CO$_2$). Media were changed every 48 hours until the cells were confluent. Upon confluency, the cells were detached by trypsin (0.05% trypsin EDTA, 5 min).

HEK293 cells stably expressing homogeneous populations of $\alpha_{1A}$-, $\alpha_{1B}$- and $\alpha_{1D}$-ARs were grown in 150 cm$^2$ Corning flasks with Dulbecco's modified Eagle's medium supplemented with 10% fetal bovine serum, 2 mM glutamine, penicillin (100 units/ml) and streptomycin (100 µg/ml). The flasks were incubated at 37° C. (5% CO$_2$). Media were changed every 48 hours until the cells were confluent. Upon confluency, the cells were detached by gentle scraping.

Radioligand Binding Assays

Radioligand binding studies were conducted in CHO cells expressing homogeneous populations of $\alpha_{2A}$-, $\alpha_{2B}$- and $\alpha_{2C}$-ARs. Similar studies were performed in HEK293 cells expressing homogeneous populations of $\alpha_{1A}$-, $\alpha_{1B}$- and $\alpha_{1D}$-ARs. Briefly, CHO cells were harvested using Ham's F-12 media following trypsinization while HEK293 cells were detached by simple scraping. The cell suspension was centrifuged and the pellet re-suspended in Tris-EDTA buffer, pH 7.4. The competition binding assays were performed in duplicate by incubating ~50,000 cells with [$^3$H]rauwolscine (0.1 µCi, 0.7 nM) for human $\alpha_{2A}$-, $\alpha_{2B}$- and $\alpha_{2C}$-ARs and [$^3$H]prazosin (0.1 µCi, 0.7 nM) for human $\alpha_{1A}$-, $\alpha_{1B}$- and $\alpha_{1D}$-ARs. The assays were conducted in a final volume of 2 ml. Non-specific binding was determined in the presence of 10 µM phentolamine. The percentage of specific binding was determined by dividing the difference between the total bound (dpm) and nonspecific bound (dpm) by the total bound (dpm). Specific binding was about 95% of the total binding. Inhibition of specific binding by the competitors was determined using varying concentrations of the analogs. Incubations were terminated at 60 minutes by rapid filtration over Whatman GF/C glass fiber filters (Maidstone, UK) using a cell harvester (Brandel Inc., Gaithersburg, Md.). The filter discs were washed three times with Tris-EDTA buffer, pH 7.4, at 4° C. The radioactivity was quantified by using a Packard TRI-CARB 2900 TR Liquid Scintillation Analyzer (Packard Instrument Company, CT, USA) and data analyzed using GraphPad Prism (GraphPad Software, San Diego, Calif., USA).

Scatchard analyses were carried out using varying concentrations of selected radioligands to determine their affinities ($K_D$) and maximal binding characteristics ($B_{max}$). The saturation binding of [$^3$H]rauwolscine to human $\alpha_{2A}$-, $\alpha_{2B}$- and $\alpha_{2C}$-ARs and [$^3$H]prazosin to human $\alpha_{1A}$-, $\alpha_{1B}$- and $\alpha_{1D}$-ARs was conducted in a final volume of 1 ml. Non-specific binding for the $\alpha_1$- and $\alpha_2$-ARs was determined in the presence of 10 µM phentolamine and 10 µM yohimbine, respectively. The total and nonspecific binding for each concentration was determined in triplicate. The specific binding, at each concentration of the radioligand, was established and plotted as bound ligand versus bound/free ligand and the corresponding $K_D$ and $B_{max}$ values calculated on each human α-AR subtype. Data are expressed as the mean±S.E.M. of n=6-9 experiments. The experimentally determined $K_D$ (nM) and $B_{max}$ (pmoles/mg protein) values (mean±SEM, n=6-9 experiments) of the radioligands on the AR subtypes were as follows: [$^3$H]rauwolsine: $\alpha_{2A}$=1.93±0.12 and 8.20±0.71; $\alpha_{2B}$=1.45±0.08 and 1.64±0.10; $\alpha_{2C}$=0.32±0.01 and 1.20±0.13 in CHO cells; and [$^3$H]prazosin: $\alpha_{1A}$=0.22±0.008 and 0.56±0.01; $\alpha_{1B}$=0.24±0.01 and 1.59±0.10; $\alpha_{1D}$=0.14±0.01 and 0.46±0.04 in HEK293 cells.

Cyclic AMP Response Element-Luciferase Reporter Gene Assay

To verify that the observed binding affinities of yohimbine and its selected tethered monomeric analogs correlate with the functional responses in the $\alpha_2$-ARs, functional responses of selected ligands were determined by using six copies of a cAMP response element-luciferase reporter gene construct (6

CRE-LUC, pADneo2-C6-BGL). The reporter gene assays were conducted in CHO cells expressing the human $\alpha_{2A}$- and $\alpha_{2C}$-AR subtype. The cells were grown to confluence, upon which they were isolated and electroporated in the presence of the plasmid. The transfection procedure employed was the same as described previously in CHO cells (Lalchandani et al., "Yohimbine Dimers Exhibiting Selectivity for the Human $\alpha_{2C}$-AR Subtype," *J. Pharmcol. Exp. Ther.* 303:979-984 (2002); Vansal et al., "An Efficient Cyclic AMP Assay for the Functional Evaluation of β-Adrenergic Receptor Ligands," *J. Recept. Signal Transduct. Res.* 19:853-863 (1999), each of which is hereby incorporated by reference in its entirety). Cells were transiently transfected with the 6 CRE-LUC plasmid (5 μg/100 μl of cell suspension) using electroporation at 150 V, 70 ms, single pulse. Transfected cells were plated into a 96-well microplate at a density of approximately 50,000 cells per well and allowed to grow for 20 hours. Fixed concentrations of the nonselective $\alpha_2$-AR agonist, medetomidine (Virtanen et al., "Characterization of the Selectivity, Specificity and Potency of Medetomidine as an $\alpha_2$-Adrenoceptor Agonist," *Eur. J. Pharmcol.* 150:9-14 (1988), which is hereby incorporated by reference in its entirety) that produced a submaximal inhibition of the forskolin response (0.01 μM and 1 μM for the $\alpha_{2A}$- and $\alpha_{2C}$-ARs, respectively), were added directly to the medium 20 minutes prior to the addition of forskolin (3-5 μM) and then allowed to incubate for 4 hours. Selected ligands were tested for antagonist activity and added 20 minutes prior to the addition of the medetomidine. The media was then aspirated, the cells lysed, and the luciferase activity determined using the LucLite assay kit (Packard Biosciences, Meriden, Conn., USA). Changes in light production were measured by a Packard Topcount Luminescence Counter (Packard Biosciences, Meriden, Conn., USA) after adding luciferin. Medetomidine inhibited the forskolin-induced cAMP changes by approximately 50-70% in each of the two subtypes, and the antagonist effects of yohimbine and selected tethered monomeric yohimbine analogs were determined by their ability to reverse the medetomidine action. The $EC_{50}$ values of yohimbine and its analogs for the reversal of the medetomidine action against forskolin-induced cAMP responses at the human $\alpha_{2C}$-AR were calculated using GraphPad Prism™ software (GraphPad Software, San Diego, Calif., USA) and expressed as the mean±S.E.M. of n=4 or more experiments.

Data Accumulation and Statistical Analyses

For ligand binding studies in cell lines, varying concentrations of each of the compounds, ranging from $10^{-12}$ to $10^{-5}$ M, were added in duplicate within each experiment, and the individual molar inhibitory concentration-50 ($IC_{50}$) values were determined using GraphPad Prism™. The displacement curves were plotted using a standard slope factor of 1.0; and the $K_i$ values of the competing ligands were determined using the equation $pKi = -\log K_i$ (where $K_i$ was calculated according to Cheng and Prusoff, "Relationship Between the Inhibition Constant ($K_1$) and the Concentration of Inhibitor which Causes 50 Percent Inhibition ($I_{50}$) of an enzymatic Reaction," *Biochem. Pharmacol.* 22:3099-3108 (1973), which is hereby incorporated by reference in its entirety). Individual $pK_i$ values are used to determine whether there are significant differences among means of the analogs on the three α2-AR subtypes. The higher the $pK_i$ value, the higher the potency ($K_i$) for the drug. A conversion of the $pK_i$ to a nM $K_i$ scale would be as follows: 9.0=1 nM, 8.0=10 nM, 7.0=100 nM, 6.0=1000 nM, and so forth. The final data are presented as mean±SEM of n=4 or more experiments.

Differences between means of binding affinities and functional responses for individual ligands on the AR subtypes were done by ANOVA and Tukey's post hoc analysis test. When two means were compared, statistical analyses were done using Student's T-test. Values were considered to be statistically significant when P<0.05.

Example 1

Synthesis of Yohimbine Derivatives

The derivatives of yohimbine were synthesized by coupling yohimbinic acid with reagents having free amino groups under standard peptide coupling conditions. 1,3-Dicyclohexylcarbodiimide (DCC) was used as the coupling agent and N-hydroxybenzotriazole (HOBT) was used as an additive to catalyze the reaction and to suppress the epimerization at C-16.

Accordingly, the yohimbine monomeric analogs were prepared as shown in Scheme 1 (FIG. 2A). The yohimbine monomeric analogs 9 and 11 were prepared by the deprotection of 6 using HCl in ether and by the catalytic hydrogenation of 10 using 10% PD/C in ethyl acetate, respectively. Attempts to prepare compound 11 by ester hydrolysis were successful, although isolation was not. This prompted its preparation via the benzyl derivative 10 followed by reduction. The structures of all the yohimbine monomeric analogs synthesized were characterized by $^1$H NMR, MS and CHN analyses. The mono-N-protected-1,3-diaminopropanes 16 and 17 were prepared as illustrated in Scheme 2 (FIG. 2B) (Lee et al., "An efficient and practical method for the synthesis of mono-N-protected α,ω-diaminoalkanes," *Tetrahedron Lett.* 42:2709-2711 (2001), which is hereby incorporated by reference in its entirety), whereas intermediate 21 was prepared by the deprotection of intermediate 20 with TFA at 0° C. in methylene chloride medium. Intermediate 20 was prepared as the coupled product of glycine methyl ester hydrochloride 18 and N-t-Boc glycine 19 under the conditions shown in FIG. 2B.

Example 2

Radioligand Binding Assay

Radioligand binding analyses of yohimbine (1), yohimbinic acid (2), the n=3 (3) and n=24 (4) of yohimbine dimers, and tethered monomeric yohimbine analogs (5-11) were performed in CHO cells stably expressing homogeneous populations of human $\alpha_{2a}$-, $\alpha_{2b}$- and $\alpha_{2c}$-ARs. The competition binding assays were performed with [$^3$H]rauwolscine (0.1 μCi, 0.7 nM) and non-specific binding was determined in the presence of 10 μM phentolamine. $K_i$ and $IC_{50}$ values were calculated as described above.

Structures of all compounds are provided in FIGS. 1 and 3. The binding affinities, expressed as $pK_i$ values, for each of the compounds on the three human α2-AR subtypes are presented in Table 1 below.

TABLE 1

Binding Affinities ($pK_i$) of Compounds 1-11 on Human $\alpha_{2A}$-, $\alpha_{2B}$-, and $\alpha_{2C}$-AR Subtypes Stably Expressed in CHO cells

| Compound | $\alpha_{2A}$ $pK_i$ ± SEM | $\alpha_{2B}$ $pK_i$ ± SEM | $\alpha_{2C}$ $pK_i$ ± SEM |
|---|---|---|---|
| Yohimbine (1) | 8.75 ± 0.03[a] | 8.14 ± 0.04 | 9.01 ± 0.03[b] |
| Yohimbinic acid (2) | 6.21 ± 0.12[a] | 7.87 ± 0.18 | 7.71 ± 0.05[d] |

TABLE 1-continued

Binding Affinities (pK$_i$) of Compounds 1-11 on Human $\alpha_{2A}$-, $\alpha_{2B}$-, and $\alpha_{2C}$-AR Subtypes Stably Expressed in CHO cells

| Compound | $\alpha_{2A}$ pK$_i$ ± SEM | $\alpha_{2B}$ pK$_i$ ± SEM | $\alpha_{2C}$ pK$_i$ ± SEM |
|---|---|---|---|
| Yohimbine n = 3 dimer (3) | 6.80 ± 0.02[a] | 6.22 ± 0.03 | 8.05 ± 0.04[b] |
| Yohimbine n = 24 dimer (4) | 5.79 ± 0.06[c] | 5.85 ± 0.08 | 6.76 ± 0.03[b] |
| Yohimbine monoglycine ester (5) | 7.47 ± 0.02[c] | 7.44 ± 0.02 | 8.07 ± 0.03[b] |
| Yohimbine diglycine ester (6) | 7.33 ± 0.01[a] | 6.62 ± 0.03 | 8.28 ± 0.07[b] |
| Yohimbine benzyl carbamate alkyl amine (7) | 7.91 ± 0.07[a] | 7.17 ± 0.09 | 8.94 ± 0.11[b] |
| Yohimbine t-butyl carbamate alkyl amine (8) | 7.96 ± 0.07[a] | 6.98 ± 0.04 | 8.50 ± 0.07[b] |
| Yohimbine alkyl amine (9) | 6.64 ± 0.03[a] | 5.64 ± 0.09 | 7.50 ± 0.04[b] |
| Yohimbine benzyl carboxy alkyl amine (10) | 7.56 ± 0.06[a] | 5.89 ± 0.06 | 9.19 ± 0.02[b,c] |
| Yohimbine carboxy alkyl amine (11) | 6.03 ± 0.09[a] | 6.78 ± 0.16 | 8.50 ± 0.07[b] |

[a]Mean pKi value on the $\alpha_{2A}$-AR is significantly different from the mean pKi value on the $\alpha_{2B}$- and $\alpha_{2C}$-ARs.
[b]Mean pKi value on the $\alpha_{2C}$-AR is significantly different from the mean pKi value on the $\alpha_{2A}$- and $\alpha_{2B}$-ARs.
[c]Mean pKi value on the $\alpha_{2A}$-AR is significantly different from the mean pKi value on the $\alpha_{2C}$-AR.
[d]Mean pKi value on the $\alpha_{2C}$-AR is significantly different from the mean pKi value on the $\alpha_{2A}$-AR.
[e]Mean pKi value of the analog is significantly different from the mean pKi value of yohimbine on same AR.

As given in Table 1, with the exception of yohimbinic acid (2), each of the other compounds possessed a higher pK$_i$ value (and higher potency) for the human $\alpha_{2C}$-AR subtype. The potencies of these analogs were statistically significant (P<0.05) as compared to their corresponding means at the human $\alpha_{2A}$-AR and $\alpha_{2b}$-AR subtypes. Each of the newly synthesized monomeric yohimbine analogs possessed a significant selectivity for the $\alpha_{2C}$-AR, and several of these derivatives (6-8, 10, 11) gave higher potency values than the two dimeric analogs (3 and 4) on this subtype.

The binding potencies (K$_i$ values) of the various dimeric and monomeric yohimbine analogs is provided in Table 2 below.

TABLE 2

Binding Data (K$_i$) of Compounds 1-11 on Human $\alpha_{2A}$-, $\alpha_{2B}$-, and $\alpha_{2C}$-AR Subtypes Stably Expressed in CHO Cells

| Compound | K$_i$ (nM) | | |
|---|---|---|---|
| | $\alpha_{2A}$ | $\alpha_{2B}$ | $\alpha_{2C}$ |
| 1 | 1.78 | 7.24 | 0.98 |
| 2 | 616 | 13.4 | 19.4 |
| 3 | 158 | 602 | 8.91 |
| 4 | 1621 | 1412 | 173 |
| 5 | 33.8 | 36.3 | 8.51 |
| 6 | 46.7 | 239 | 5.24 |
| 7 | 12.3 | 67.6 | 1.14 |
| 8 | 11.7 | 105 | 3.16 |
| 9 | 229 | 2290 | 31.6 |
| 10 | 27.5 | 1290 | 0.64 |
| 11 | 933 | 165 | 3.16 |

The effects produced by the introduction of functional groups in the side chain at C-16 of yohimbine were noticeable as seen in the changes of the K$_i$ values (see Table 2). In general, a comparison of the K$_i$ values clearly points out that the yohimbine dimer (4) has weak affinity (K$_i$=173 nM) for the human $\alpha_{2C}$-ARs as compared to dimer 3 and the other monomeric analogs. Results show that among the monomeric derivatives, compound 10 exceeds the binding affinity of the parent compound yohimbine 1 towards $\alpha_{2C}$-ARs. Compounds 7, 8, and 11 possessed comparable affinities to the parent compound, while 5 and 6 displayed relatively lower binding potency than yohimbine. The introduction of a carboxyl group at the side chain led to derivative 11, a structure similar to yohimbinic acid 2 that surprisingly surpasses the affinity of 2 for the human $\alpha_{2C}$-ARs. The amino analog 9 exhibited significantly weaker affinity. The above results demonstrate that a second pharmacophore is not essential to obtain $\alpha_{2C}$-AR selectivity; instead, selectivity and binding affinity depends on the nature of the substituent in the side chain.

The rank order of binding affinities exhibited by yohimbine (1) on the human $\alpha_2$-AR subtypes was $\alpha_{2C} \geq \alpha_{2A} > \alpha_{2B}$, with a 2- and 7-fold higher binding affinity for the $\alpha_{2C}$- versus the $\alpha_{2A}$- and $\alpha_{2B}$-AR. Interestingly, studies with yohimbinic acid (2) revealed that this compound exhibited a greatly decreased binding potency at the $\alpha_{2A}$- (345-fold) versus the $\alpha_{2B}$- (2-fold) and the $\alpha_{2C}$-AR (20-fold), as compared to yohimbine. Further, it was equipotent in binding to the $\alpha_{2B}$- and $\alpha_{2C}$-AR, and its binding at the $\alpha_{2B}$-AR was 46-fold greater than its binding at the $\alpha_{2A}$-AR. FIGS. 4A-B show the binding displacement curves for yohimbine (1) (4A) and yohimbinic acid (2) (4B) at the three $\alpha_2$-AR receptor subtypes. The n=3 (3) and n=24 (4) dimeric analogs were 18- and 68-fold and 9- and 8-fold selective in binding to the $\alpha_{2C}$- vs. $\alpha_{2A}$- and $\alpha_{2B}$-subtypes (Table 1). All of the tethered monomeric yohimbine analogs (5-11) exhibited significantly higher binding affinities at the $\alpha_{2C}$- vs. $\alpha_{2A}$- and $\alpha_{2B}$-AR subtypes (see Table 1). In particular, the benzyl carbamate alkyl amine (7), t-butyl carbamate alkyl amine (8), benzyl carboxy alkyl amine (10), and carboxy alkyl amine (11) analogs possessed binding affinities comparable to the parent molecule, yohimbine (1), at the $\alpha_{2C}$-AR (Table 2). The alkyl amine analog (9), however, was 32-fold less potent in binding to the $\alpha_{2C}$-AR as compared to yohimbine (1). Also, it was 129- and 316-fold less potent in binding to the $\alpha_{2A}$- and $\alpha_{2B}$-AR subtypes in comparison with yohimbine. The monoglycine ester analog (5) showed a 4-fold higher binding affinity at the $\alpha_{2C}$- versus the $\alpha_{2A}$- and $\alpha_{2B}$-ARs (Table 1). The diglycine ester analog (6) was 9- and 46-fold selective in binding to the $\alpha_{2C}$- versus the $\alpha_{2A}$- and $\alpha_{2B}$-ARs (Table 1). The benzyl carbamate alkyl amine analog (7) and the t-butyl carbamate alkyl amine analog (8) were 11- and 59-fold and 3- and 33-fold selective in binding to the $\alpha_{2C}$- versus the $\alpha_{2A}$- and $\alpha_{2B}$-ARs, respectively (Table 1). The benzyl carboxy alkyl amine analog (10) and the carboxy alkyl amine analog (11) exhibited a 43- and 1995-fold and 295- and 54-fold selectivity in binding to the $\alpha_{2C}$- vs. $\alpha_{2A}$- and $\alpha_{2B}$-ARs, respectively (Table 1). FIGS. 4C-D illustrate the binding displacement curves for the benzyl carboxy alkyl amine analog (10) and the carboxy alkyl amine analog (11) at the $\alpha_{2A}$-, $\alpha_{2B}$-, $\alpha_{2C}$-AR subtypes, respectively. The alkyl amine analog (9) was 7- and 72-fold selective in binding to the $\alpha_{2C}$- versus the $\alpha_{2A}$- and $\alpha_{2B}$-ARs (Table 1).

As has been observed with the yohimbine dimers (Lalchandani et al., "Yohimbine Dimers Exhibiting Selectivity for the Human $\alpha_{2C}$-AR Subtype," *J Pharmacol Exp Ther* 303: 979-984 (2002), which is hereby incorporated by reference in its entirety), all of the tethered monomeric yohimbine analogs, with the exception of the monoglycine ester (5) and the carboxy alkyl amine (11) analogs, displayed lower binding affinities at the $\alpha_{2B}$- versus the $\alpha_{2A}$- and $\alpha_{2C}$-AR. The monoglycine ester analog (5) was equipotent in binding to the $\alpha_{2A}$- and $\alpha_{2B}$-AR, whereas the carboxy alkyl amine analog (11) was 6-fold more potent in binding to the $\alpha_{2B}$- versus the $\alpha_{2A}$-AR (Table 1).

The binding affinities of yohimbine (1) and the two selected tethered monomeric analogs viz. the benzyl carbamate alkyl amine (7) and alkyl amine (9) analogs, were determined in HEK293 cells stably expressing homogeneous populations of human $\alpha_{1A}$-, $\alpha_{1B}$- and $\alpha_{1D}$-ARs. Yohimbine and the selected monomeric analogs were found to bind with low affinities at all three $\alpha_1$-subtypes (Table 3 below). The binding affinities of yohimbine (1), the benzyl carbamate alkyl amine (7), and the alkyl amine (9) analog for the $\alpha_{2C}$-AR subtype were at least 224-, 562- and 100-fold greater than those on the $\alpha_1$-AR subtypes, respectively (comparing data in Tables 1 and 3). Taken collectively, the data confirm the binding selectivity of these ligands for the $\alpha_{2C}$-AR subtype.

TABLE 3

Binding Affinities ($pK_i$) of Compounds 1, 7, and 9 on Human $\alpha_{1A}$-, $\alpha_{1B}$-, and $\alpha_{1D}$-AR Subtypes that are Stably Expressed in HEK293 cells

| Compound | $\alpha_{1A}$ $pK_i$ ± SEM | $\alpha_{1B}$ $pK_i$ ± SEM | $\alpha_{1D}$ $pK_i$ ± SEM |
| --- | --- | --- | --- |
| Yohimbine (1) | 6.66 ± 0.02[a] | 6.03 ± 0.08[b] | 6.52 ± 0.15 |
| Yohimbine benzyl carbamate alkyl amine (7) | 6.19 ± 0.16 | 6.16 ± 0.20 | 6.02 ± 0.22 |
| Yohimbine alkyl amine (9) | Less than 50% specific inhibition at 10 µM | less than 50% specific inhibition at 10 µM | less than 50% specific inhibition at 10 µM |

[a]Mean pKi value on the $\alpha_{1A}$-AR subtype is significantly different from the mean pKi value on the $\alpha_{1B}$-AR subtype.
[b]Mean pKi value on the $\alpha_{1B}$-AR subtype is significantly different from the mean pKi value on the $\alpha_{1D}$-AR subtype.

Example 3

Cyclic AMP Response Element-Luciferase Reporter Gene Assay

The functional responses of yohimbine and selected tethered monomeric analogs in the human $\alpha_{2A}$- and $\alpha_{2C}$-AR expressing CHO cells were determined using six copies of a cAMP response element-luciferase reporter gene construct (6 CRE-LUC, pADneo2-C6-BGL).

The assays with both $\alpha_{2A}$- and $\alpha_{2C}$-ARs were conducted using the non-subtype selective $\alpha_2$-AR agonist, medetomidine, to block the cAMP changes induced by the adenyl cyclase activator, forskolin. The concentration of forskolin (3-5 µM) for the assays was chosen such that it produced at least a 7- to 10-fold increase over basal levels. Basal values (solvent control) were subtracted from the forskolin values and the resulting forskolin response was used as 100%. Similarly, basal values were subtracted from all other values obtained with ligands, and the data expressed as a percentage luciferase response relative to that of forskolin alone.

Preliminary experiments with CHO cells stably expressing the $\alpha_{2A}$-ARs revealed a biphasic concentration-response curve by medetomidine (FIG. 5A). As shown, medetomidine showed an inhibition of the forskolin-induced cAMP response at low concentrations (0.0001-0.01 µM), whereas higher concentrations (0.1-10 µM) reversed the inhibition of luciferase activity observed at the lower medetomidine concentrations. The maximal inhibition obtained for medetomidine was 56% at 0.01 µM. Medetomidine alone (in the absence of forskolin) increased cAMP levels by 17% when tested at a concentration of 10 µM (FIG. 5C).

In cells expressing the $\alpha_{2C}$-AR, however, medetomidine caused a concentration-dependent reduction in the forskolin-induced cAMP activity at all concentrations tested (0.01-10 µM). The maximal inhibition obtained for medetomidine was 70% at 1 µM (FIG. 5B). A higher concentration of medetomidine (10 µM) did not cause any further decrease in the forskolin-induced cAMP. Medetomidine alone (in the absence of forskolin) did not show an increase in cAMP levels when tested at a concentration of 1 µM (FIG. 5D).

For functional studies with yohimbine and selected tethered monomeric yohimbine analogs at the $\alpha_{2A}$- and $\alpha_{2C}$-ARs, the concentration of medetomidine was chosen such that it produced a sub-maximal (around 50-70%) inhibition of the forskolin response in these subtypes. From data presented in FIGS. 5A-D, the medetomidine concentration was fixed at 0.01 µM for the $\alpha_{2A}$-AR whereas it was fixed at 1 µM for the $\alpha_{2C}$-AR. The agonist ligand, medetomidine, was added directly to the medium 20 minutes prior to the addition of forskolin and then allowed to incubate for 4 hours. Tethered monomeric yohimbine analogs selected for functional testing at the $\alpha_2$-ARs included the benzyl carbamate alkyl amine (7) and the alkyl amine (9) analogs. Concentrations of yohimbine (1), the benzyl carbamate alkyl amine (7), and the alkyl amine analog (9) were fixed at 0.1, 0.1, and 1 µM, respectively for the $\alpha_{2A}$-AR assays while they were varied from 0.001 to 10 µM for the $\alpha_{2C}$-AR assays. These compounds were added 20 minutes prior to the addition of medetomidine.

On the $\alpha_{2A}$-AR, medetomidine (0.01 µM) inhibited forskolin-induced cAMP changes and the mean inhibition produced was 56±2% for n=5 experiments (FIG. 6). As noted in the graph, the mean percent inhibitions (of the medetomidine response) by yohimbine (1) (0.1 µM), the benzyl carbamate alkyl amine analog (7) (0.1 µM) and the alkyl amine analog (9) (1 µM) were 14.2%, 54% and 53%, respectively. Thus, the changes in luciferase activity produced by medetomidine were blocked by yohimbine (1) (0.1 µM). Neither of the two monomeric analogs blocked the medetomidine inhibition of forskolin-induced luciferase activity at the chosen concentrations. None of the test antagonist ligands produced agonist activity at the concentration tested (FIG. 6).

Figure 7A:
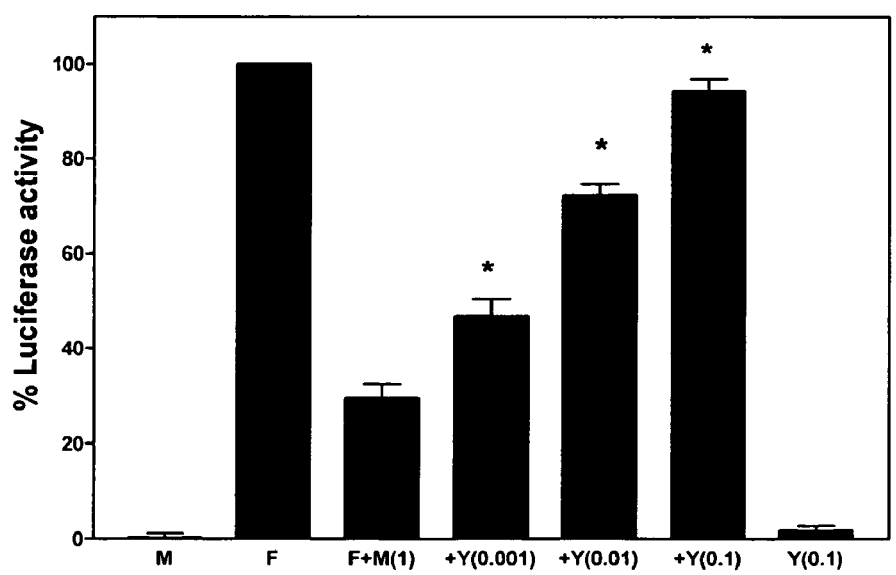
FIGS. 7A-C illustrate the reversal of medetomidine inhibition of forskolin-induced cAMP elevations, as assessed by luciferase activity, by yohimbine (7A), yohimbine benzyl carbamate alkyl amine monomer (7B), and yohimbine alkyl amine monomer (7C) on human $\alpha_{2C}$-ARs stably expressed in CHO cells. Plotted values are the mean±SEM (n=4 experiments). Structures of compounds are shown in FIGS. 1 and 3. Key: F, forskolin (3 µM); M, medetomidine (1 µM); Y, yohimbine (0.001, 0.01 and 0.1 µM); BC, yohimbine carbamate alkyl amine monomer (0.001, 0.01 and 0.1 µM); and AA, yohimbine alkyl amine monomer (0.1, 1 and 10 µM). * Indicates P<0.05 compared to F+M(1) using Student's t test.
Figure 7B:
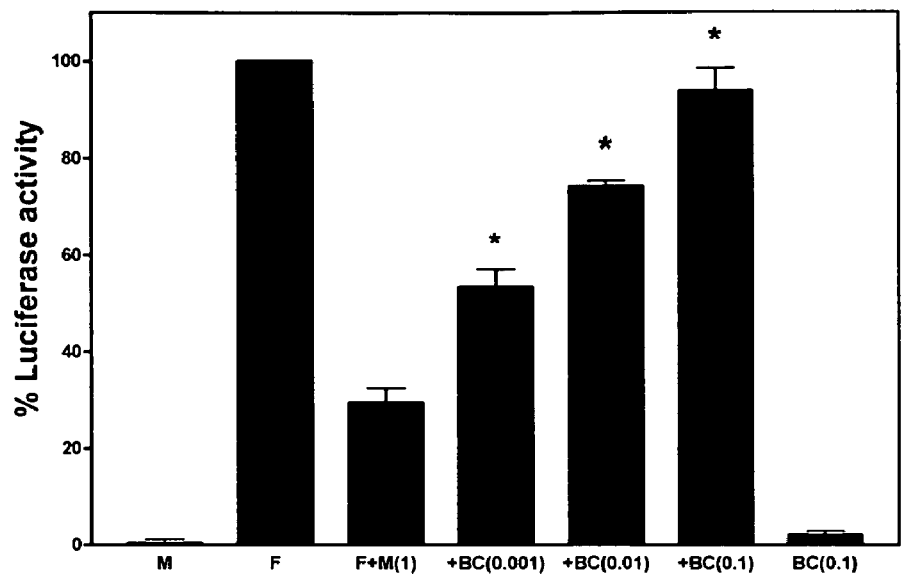
Figure 7C:
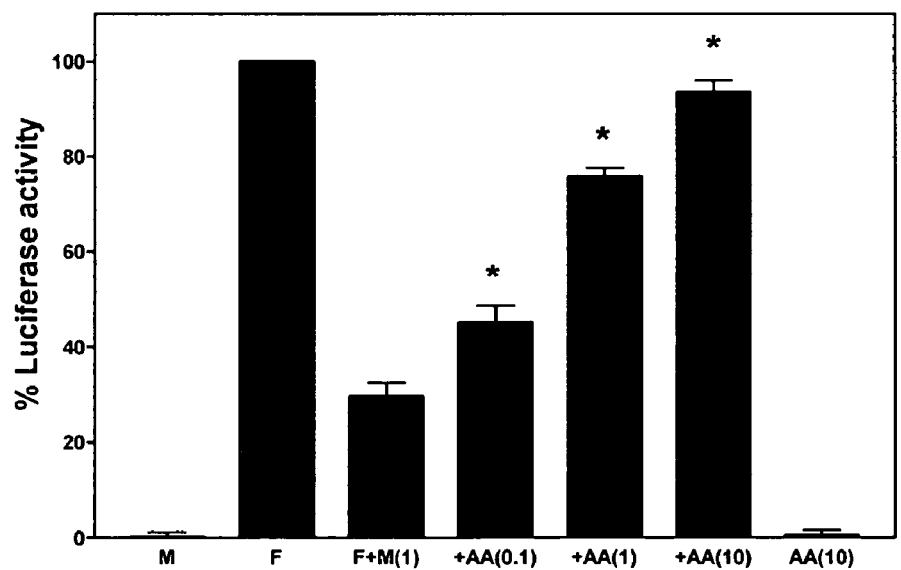

A graphical representation of the concentration-dependent effects of yohimbine (1), the benzyl carbamate alkyl amine monomer (7), and the alkyl amine monomer (9) for the reversal of the forskolin-induced cAMP changes by medetomidine at the $\alpha_{2C}$-ARs is provided in FIGS. 7A-C, respectively. As can be seen from these graphs, the mean percentage inhibition produced by medetomidine (1 µM) at the $\alpha_{2C}$-AR was 70±2% for n=4 experiments. None of the test antagonist ligands produced agonist activity at the highest concentration tested (FIGS. 7A-C).

Figure 8:
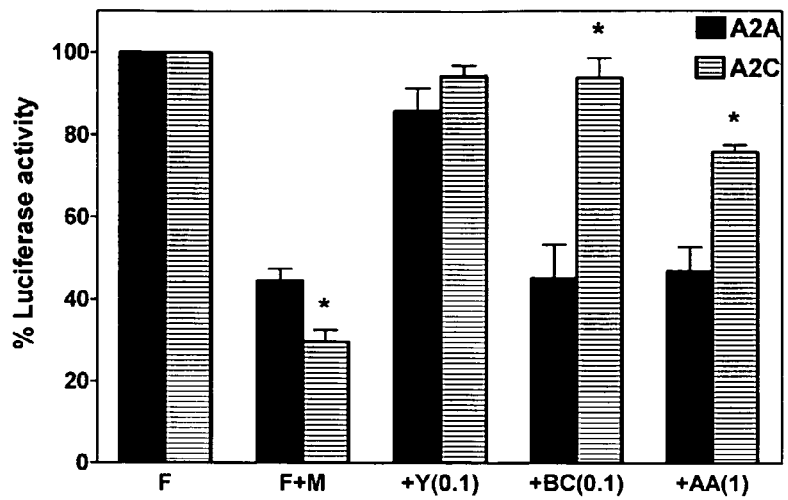
FIG. 8 shows a comparison of the ability of yohimbine and selected tethered monomeric yohimbine analogs to reverse the medetomidine inhibition of forskolin-induced cAMP elevations, as assessed by luciferase activity, on human $\alpha_{2A}$- and $\alpha_{2C}$-ARs stably expressed in CHO cells. Plotted values are the mean±SEM (n=4-5 experiments). Structures of compounds are shown in FIGS. 1 and 3. Key: F, forskolin (3-5 µM); M, medetomidine; Y, yohimbine (0.1 µM); BC, yohimbine benzyl carbamate alkyl amine monomer (0.1 µM); and AA, yohimbine alkyl amine monomer (1 µM). The concentration of forskolin (3-5 µM) was chosen such that it produced at least a 7- to 10-fold increase over basal levels. The concentration of medetomidine was chosen such that it produced at least a 50% inhibition of the forskolin-induced cAMP response. The mean inhibition produced in case of the $\alpha_{2A}$-ARs was 56±2% for n=5 experiments whereas at the $\alpha_{2C}$-ARs, the mean inhibition was 70±2% for n=4 experiments. * Indicates response at the $\alpha_{2C}$-ARs is different from the response at $\alpha_{2A}$-ARs (P<0.05 using Student's t test).

A comparison of the experimentally determined functional antagonist activities for yohimbine and the selected tethered monomeric yohimbine analogs at human $\alpha_{2A}$- and $\alpha_{2C}$-ARs stably expressed in CHO cells is given in FIG. 8. As shown, significant differences were observed in the abilities of the benzyl carbamate alkyl amine monomer (7) and the alkyl amine monomer (9) to reverse the medetomidine inhibition of forskolin-induced cAMP elevations at the $\alpha_{2A}$- and $\alpha_{2C}$-AR subtypes, when used at the same concentration. Concentrations used were: yohimbine (1) (0.1 µM), yohimbine benzyl carbamate alkyl amine monomer (7) (0.1 µM), and yohimbine alkyl amine monomer (9) (1 µM). It is important to note here that the two monomeric analogs were able to reverse the medetomidine-inhibition of the forskolin response on the $\alpha_{2C}$-AR subtype, but not on the $\alpha_{2A}$-AR subtype. Further, in spite of the inhibition produced by medetomidine being less in the $\alpha_{2A}$- (56±2%) versus the $\alpha_{2C}$-AR subtype (70±2%), blockade of the medetomidine responses were only observed with yohimbine on the $\alpha_{2A}$-AR. Taken collectively, these data indicate the $\alpha_{2C}$- versus $\alpha_{2A}$-AR selectivity of the selected tethered monomeric yohimbine analogs.

Table 4 (below) shows the $pEC_{50}$ values of yohimbine and its analogs for the reversal of the medetomidine action against forskolin-induced cAMP responses at the humans $\alpha_{2C}$-AR, along with their binding affinities (pKi values) at the same receptor subtype. As seen from Table 4, the functional potencies of yohimbine and the benzyl carbamate alkyl amine analog (7) as the $\alpha_{2C}$-ARs were not found to be statistically different from the experimentally determined binding affinities. Also, the rank order of functional and binding potencies for the three compounds remained the same: yohimbine benzyl carbamate alkyl amine (7)≧yohimbine (1)>yohimbine alkyl amine (9).

TABLE 4

$EC_{50}$ Values of Compounds 1, 7, and 9 for Reversing Medetomidine Effects on Forskolin-induced cAMP Elevations in CHO Cells Stably Expressing the $\alpha_{2C}$-ARs

| Compound | $pEC_{50}$ | $EC_{50}$(nM) | pKi | Ki (nM) |
| --- | --- | --- | --- | --- |
| Yohimbine (1) | 8.90 ± 0.15[a] | 1.25 | 9.01 ± 0.03[b] | 0.97 |
| Yohimbine benzyl carbamate alkyl amine (7) | 9.31 ± 0.24[a] | 0.48 | 8.94 ± 0.11[b] | 1.1 |
| Yohimbine alkyl amine (9) | 6.87 ± 0.11 | 134 | 7.50 ± 0.04 | 31.5 |

[a]Mean $pEC_{50}$ of the analog is significantly different from the mean $pEC_{50}$ value of yohimbine alkyl amine.
[b]Mean pKi of the analog is not significantly different (P > 0.05) from its mean $pEC_{50}$ value.

Discussion of Examples 1-3

GPCRs, traditionally considered to function as monomeric proteins, have now been proposed to exist as dimers or even higher-structure oligomers (Angers et al., "Dimerization: An Emerging Concept for G Protein-coupled Receptor Ontogeny and Function," *Annu Rev Pharmacol Toxicol* 42:409-435 (2002), which is hereby incorporated by reference in its entirety). The physiological significance of such dimerization and its implications in ligand pharmacology and, potentially, for drug design remain to be fully understood. Yet, there have been efforts to improve potency and/or subtype-selectivity by employing bivalent or dimeric ligands. Lalchandani et al. demonstrated that dimers of the potent and relatively nonselective $\alpha_2$-AR antagonist yohimbine, consisting of two pharmacophores linked through a spacer, exhibited a higher degree of $\alpha_2$-AR subtype-selectivity than the parent molecule (Lalchandani et al., "Yohimbine Dimers Exhibiting Selectivity for the Human $\alpha_{2C}$-AR Subtype," *J. Pharmacol. Exp. Ther.* 303:979-984 (2002), which is hereby incorporated by reference in its entirety). The study employed the bivalent ligand approach that is based on the concept that a bivalent ligand would first undergo univalent binding followed by binding of the second pharmacophore to a recognition site on a neighboring receptor. Thus, the bivalent ligand would exhibit a greater potency than that derived from the sum of its monovalent counterparts (Portoghese, 2000 Alfred Burger Award Address in Medicinal Chemistry, "From Models to Molecules: Opioid Receptor Dimers, Bivalent Ligands, and Selective Opioid Receptor Probes," *J. Med. Chem.* 44:2259-2269 (2001), which is hereby incorporated by reference in its entirety). In the yohimbine dimer study, the addition of methylene and methylene-diglycine spacer linkages produced analogs that were potent and selective $\alpha_{2C}$-AR ligands. It was proposed that one pharmacophore (or one yohimbine molecule) binds to the ligand receptor site, while the second pharmacophore may bind to either (i) an adjacent site of the ligand binding pocket, transmembrane domain (TMD), an extracellular loop of the same receptor; or (ii) a ligand binding site or a recognition site on a neighboring receptor. With shorter spacer arms, however, an interaction of the second pharmacophore with an adjacent receptor molecule (dimer) seems less probable. Interestingly, none of the analogs in the yohimbine dimer series surpassed the affinity of yohimbine.

The compounds of the present invention demonstrated, even in the absence of the second pharmacophore (i.e., the second yohimbine molecule present in the dimer compounds 3 and 4), that appendages or tethers of varying nature and composition retained high binding potencies at the human $\alpha_{2C}$-AR. In fact, the benzyl carboxy alkyl amine analog (10) displayed a greater binding affinity at the $\alpha_{2C}$-AR than yohimbine (Table 1). This suggests that high binding affinities, previously observed with the dimeric ligands, may not be attributable to receptor dimerization and clustering as earlier proposed (Lalchandani et al., "Yohimbine dimers Exhibiting Selectivity for the Human $\alpha_{2C}$-AR Subtype," *J. Pharmacol. Exp. Ther.* 303:979-984 (2002), which is hereby incorporated by reference in its entirety).

In the yohimbine dimer sires, the n=3 (3) and n=24 (4) dimeric analogs were 32- and 355-fold and 82- and 776-fold more selective in binding to the $\alpha_{2C}$- versus $\alpha_{2A}$- and $\alpha_{2B}$-AR respectively (Lalchandani et al., "Yohimbine Dimers Exhibiting Selectivity for the Human $\alpha_{2C}$-AR Subtype," *J. Pharmacol. Exp. Ther.* 303:979-984 (2002), which is hereby incorporated by reference in its entirety). Thus, compound 4 was more selective than compound 3 in binding to the $\alpha_{2C}$-AR. However, functional assay results from the same study reported compound 3 to be more potent as well as more $\alpha_{2C}$-AR selective than compound 4. The above data differs in that compound 3 and compound 4 showed only 18- and 68-fold and 9- and 8-fold selective in binding to the $\alpha_{2C}$- versus the $\alpha_{2A}$- and $\alpha_{2B}$-AR, respectively, indicating the n=3 (3) dimer to be more $\alpha_{2C}$-selective than the n=24 (4) dimer. The binding data for these two compounds from the present study is in agreement with their functional data reported previously (Lalchandani et al., "Yohimbine Dimers Exhibiting Selectivity for the Human $\alpha_{2C}$-AR Subtype," *J. Pharmacol. Exp. Ther.* 303:979-984 (2002), which is hereby incorporated by reference in its entirety). Hence, the design of the tethered monomeric yohimbine analogs was structured using the n=3 yohimbine dimer as a standard.

The data presented above for yohimbine (1) (Table 1; FIG. 4A) agrees with that reported in the literature (Lalchandani et al., "Yohimbine Dimers Exhibiting Selectivity for the Human $\alpha_{2C}$-AR Subtype," *J. Pharmacol. Exp. Ther.* 303:979-984 (2002),; Bylund et al., "Pharmacological Characteristics of $\alpha_2$-Adrenergic Receptors: Comparison of Pharmacologically Defined Subtypes with Subtypes Identified by Molecular Cloning," *Mol. Pharmacol.* 42:1-5 (1992), each of which is hereby incorporated by reference in its entirety). Also evaluated for binding to the $\alpha_2$-ARs was yohimbinic acid (2), a non-tethered structural analog of yohimbine. Interestingly, there are no reports published in the literature on the interaction of yohimbinic acid with the ARs. Data presented above showed that a single structural change in the yohimbine molecule (changing the methyl ester at the C-16 carboxyl of yohimbine to an acid functionality), yielding yohimbinic acid, had a significant impact on its binding affinities at the $\alpha_2$-AR subtypes. Yohimbinic acid exhibited a greatly decreased binding potency at the $\alpha_{2A}$- (345-fold) versus the $\alpha_{2B}$- (2-fold) and the $\alpha_{2C}$-AR (20-fold), as compared to yohimbine (Table 1, FIG. 4B). Further, it was equipotent in binding to the $\alpha_{2B}$- and $\alpha_{2C}$-AR, and its binding at the $\alpha_{2B}$-AR was 46-fold greater than its binding at the $\alpha_{2A}$-AR. It is noteworthy that yohimbinic acid is a selective $\alpha_{2C}$- versus $\alpha_{2A}$-AR ligand, the selectivity being around 32-fold.

Consistent with results reported previously (Lalchandani et al., "Yohimbine Dimers Exhibiting Selectivity for the Human $\alpha_{2C}$-AR Subtype," *J. Pharmacol. Exp. Ther.* 303:979-984 (2002), which is hereby incorporated by reference in its entirety), the n=3 (3) and n=24 (4) dimers did not surpass the binding affinity of yohimbine. Though all the tethered monomeric yohimbine analogs exhibited higher binding affinities at the $\alpha_{2C}$- vs. $\alpha_{2A}$- and $\alpha_{2B}$-AR subtypes (Table 1), only one of the tethered analogs, the benzyl carboxy alkyl amine analog (10), exceeded the affinity of yohimbine (1) at the $\alpha_{2C}$-AR. The benzyl carbamate alkyl amine (7), the t-butyl carbamate alkyl amine (8), and the carboxy alkyl amine (11) possessed binding affinities comparable to yohimbine at the $\alpha_{2C}$-AR. The alkyl amine monomer (9) was 32-fold less potent in binding to the $\alpha_{2C}$-AR as compared to yohimbine; however, it was 129- and 316-fold less potent in binding to the $\alpha_{2A}$- and $\alpha_{2B}$-AR subtypes in comparison with yohimbine (Table 1).

With regard to $\alpha_{2C}$-AR selectivities of the tethered monomeric analogs, the benzyl carbamate alkyl amine analog (7) and the alkyl amine analog (9) possessed affinities for the $\alpha_{2C}$-AR that were 11- and 59-fold and 7- and 72-fold greater than their binding to the $\alpha_{2A}$- and $\alpha_{2B}$-ARs, respectively. The benzyl carboxy alkyl amine analog (10) and the carboxy alkyl amine analog (11) exhibited a 43- and 1995-fold and 295- and 54-fold selectivity in binding to the $\alpha_{2C}$- vs. $\alpha_{2A}$- and $\alpha_{2B}$-ARs, respectively. Whether this enhanced $\alpha_{2C}$-AR selectivity observed with the benzyl carboxy alkyl amine analog and the carboxy alkyl amine analog represents additional interactions with basic residues in or around the ligand-binding pocket needs to be further investigated. The binding results presented herein demonstrate that several of the monomeric yohimbine analogs were more $\alpha_{2C}$-AR selective than the n=3 dimer, suggesting that the second pharmacophore is not necessary to achieve the $\alpha_2$-AR subtype selectivity with this chemical scaffold.

Using luciferase reporter gene assays, the functional antagonist activities of select compounds from this series was confirmed at the $\alpha_{2A}$- and $\alpha_{2C}$-ARs (FIGS. 5-7). Data from these assays also revealed that there is an $\alpha_{2C}$- versus $\alpha_{2A}$-AR selectivity for all of the tethered monomeric analogs tested (FIG. 8).

The above results have confirmed that tethered monomeric analogs of yohimbine can be selective and potent $\alpha_{2C}$-AR antagonists. The results also help to understand the underlying basis for the $\alpha_{2C}$-AR subtype-selectivity previously observed with the dimeric analogs. These results suggest that: (1) the second pharmacophoric group, i.e., the second yohimbinic acid molecule may not be essential for the $\alpha_{2C}$-AR subtype-selectivity previously seen with the dimeric analogs; and (2) an interaction of the second pharmacophoric group with either one of the extracellular loops on the same receptor, or with a recognition site on a neighboring receptor, an adjacent site of the ligand-binding pocket on a single receptor or an adjacent receptor molecule may not be the underlying mechanism(s) required for the observed synergy witnessed with the dimeric compounds, as proposed previously (Lalchandani et al., "Yohimbine Dimers Exhibiting Selectivity for the Human $\alpha_{2C}$-AR Subtype," *J. Pharmacol. Exp. Ther.* 303:979-984 (2002); Portoghese, 2000 Alfred Burger Award Address in Medicinal Chemistry, "From Models to Molecules: Opioid Receptor Dimers, Bivalent Ligands, and Selective Opioid Receptor Probes," *J. Med. Chem.* 44:2259-2269 (2001), each of which is hereby incorporated by reference in its entirety).

Instead, it is believed that differences in the physico-chemical properties of the amino acid residues (e.g., steric, hydrogen bonding, etc.) constituting and surrounding the putative ligand-binding domain, are unique in each subtype and this distinction can be exploited to develop receptor subtype-selectivity. An additional advantage of using the monovalent ligand approach is that, compared to the dimeric compounds, the tethered monomeric analogs would have improved physico-chemical and pharmacokinetic parameters (Lipinski et al., "Experimental and Computational Approaches to Estimate Solubility and Permeability in Drug Discovery and Development Settings," *Adv. Drug Deliv. Rev.* 23:3-25 (1997), which is hereby incorporated by reference in its entirety).

Example 4

Ex Vivo Demonstration of Yohimbine Derivative Antagonist Activity in a Vasoconstriction Model Previous research using the rat cremaster muscle model has demonstrated that $\alpha_2$-ARs are predominantly present in these microvessels (Faber, "Effect of Cooling on Microvascular Smooth and Postjunctional $\alpha$2-Adrenoreceptors," *J. Physiol.* 255:H121-130 (1988); Faber, "In situ Analysis of $\alpha$-Adreno-receptors on Arteriolar and Venular Smooth Muscle in Rat Skeletal Muscle Microcirculation," *Circ. Res.* 62:37-50 (1988), each of which is hereby incorporated by reference in its entirety. This work has demonstrated the suitability of this muscle as a good model of hypothermal activation of $\alpha_2$-ARs.

Preliminary studies performed with the mouse cremaster model using medetomidine at 25° C. and 37° C. have produced a concentration-response curve, and the $EC_{50}$ values were obtained and compared. In these preliminary studies, the $EC_{50}$ values were 2.15 and 20.4 nM at 25° C. and 37° C., respectively. At the lower temperature, a 10-fold shift of the curve (to the left) was observed. In the next step of the preliminary studies, medetomidine induced vasoconstriction was reversed by using 30, 100, and 300 nM concentrations of yohimbine, and then after washing vasoconstriction was re-induced with 30 nM medetomidine. These studies demonstrated that adrenergic sensitivity had not changed during the experiment and, further, validated the model for $\alpha_{2C}$-AR studies.

The mouse cremaster muscle will therefore be used to assess the $\alpha_{2C}$-AR antagonist activity of various compounds, e.g., compounds 7, 8, 10, and 11 using the same procedures performed with yohimbine in the preliminary studies. An assessment will be made as to the efficacy of these compounds for treating hypothermal vasoconstriction of the type found, e.g., in Raynaud's Disease.

Example 5

In Vivo Demonstration of Yohimbine Derivative Antagonist Activity in a Vasoconstriction Model Preliminary studies with the mouse cremaster muscle in vivo (at 37° C.) have demonstrated that yohimbine intravenous administration 2 mg/kg was effective to induce a 22.14±1.08 percent (n=6) increase in vessel diameter. These studies demonstrate that yohimbine is a vasodilating drug in this animal model. It is expected that this model also adequately represent the vasodilation in humans.

These studies will be repeated to assess the α$_{2c}$-AR antagonist activity of various compounds, e.g., compounds 7, 8, 10, and 11 using the same procedures performed with yohimbine as in the preliminary studies. The tests will be performed at both 37° C. and 25° C. to evaluate whether the resting diameter of the resistance vessels decreases in the absence of the compounds, i.e., the possible induction of α$_{2c}$-ARs, and whether the compounds can antagonize the vasoconstriction caused by the temperature change.

Example 6

Synthesis of Intermediate Compounds and Yohimbine Derivatives

Figure 9A:
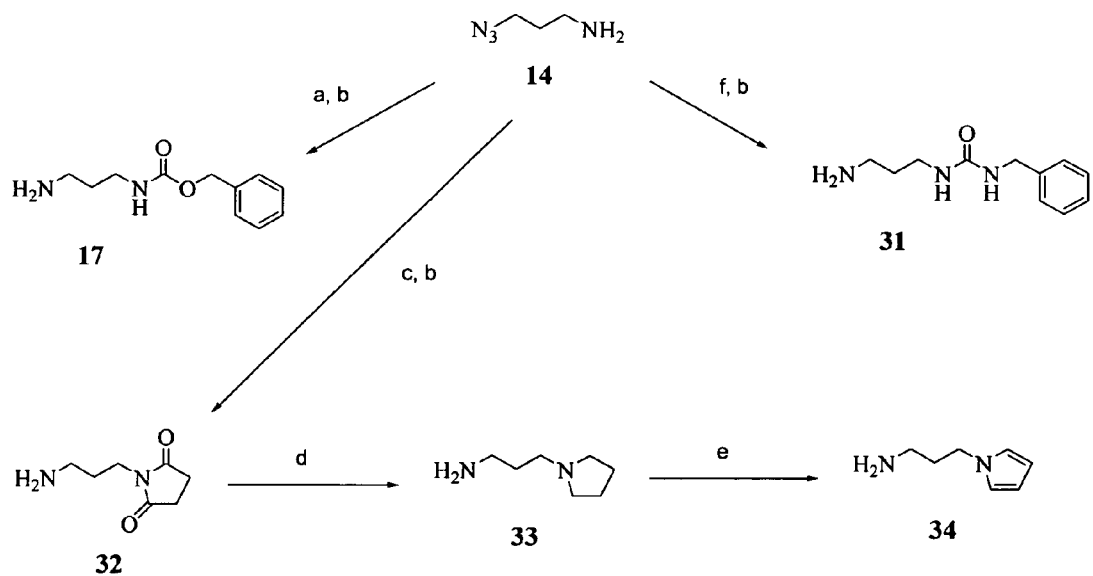
FIGS. 9A-D illustrate the synthesis of several amine-terminal starting materials (e.g., $NH_2$—$R_1$—$R_2$—$R_3$) that can be used to prepare the compounds of the present invention.

As shown in FIG. 9A, intermediates 30-34 will be prepared from 3-azidopropane-1-amine (14), which was an intermediate product described in Scheme 2 (FIG. 2B). Benzyl 3-aminopropylcarbamate (17) has been prepared as described in Example 1 (see FIG. 2B). 1-(3-aminopropyl)-3-benzylurea (31) will be prepared by treating 3-azidopropane-1-amine with benzylisocyanate followed with (Ph$_3$)P. 1-(3-aminopropyl)pyrrolidine-2,5-dione (32) will be prepared by treating 3-azidopropane-1-amine with succinic anhydride followed with (Ph$_3$)P. 1-(3-aminopropyl)pyrrolidine-2,5-dione (32) will also be converted into 3-(pyrrolidin-1-yl)propan-1-amine (33) following treatment with B$_2$H$_6$. And finally, 3-(pyrrolidin-1-yl)propan-1-amine (33) will also be converted into 3-(1H-pyrrol-1-yl)propan-1-amine (34) using palladium catalyst.

Figure 9B:
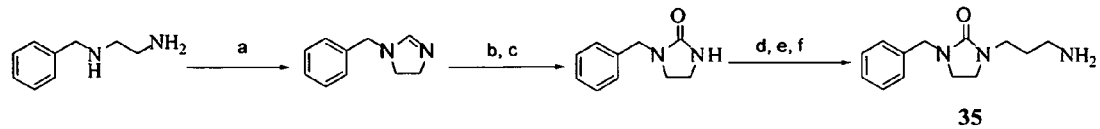

As shown in FIG. 9B (Scheme 4), the synthesis of 1-(3-aminopropyl)-3-benzylimidazolidin-2-one (35) will be performed by treating the starting material N1-benzylethane-1,2-diamine with diethoxymethoxyethane to form 1-benzyl-4,5-dihydro-1H-imidazole. The imidazole intermediate will be treated with BuLi (forming a lithiate) followed by quenching with water to form the final intermediate 1-benzylimidazolidin-2-one. Treating the imidazolidinone with NaH followed by Br—(CH$_2$)$_3$—N(SiMe$_3$)$_2$ under reducing conditions will afford the intermediate 35.

Figure 9C:
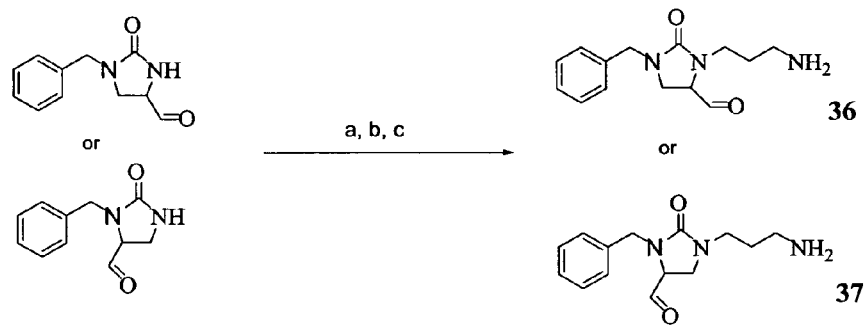

As shown in FIG. 9C (Scheme 5), using commercially available hydantoins 3-benzylimidazolidine-2,4-dione and 1-benzylimidazolidine-2,4-dione, the intermediates 3-(3-aminopropyl)-1-benzylimidazolidine-2,4-dione (36) and 1-(3-aminopropyl)-3-benzylimidazolidine-2,4-dione (37) will be prepared using the conditions described.

Figure 9D:
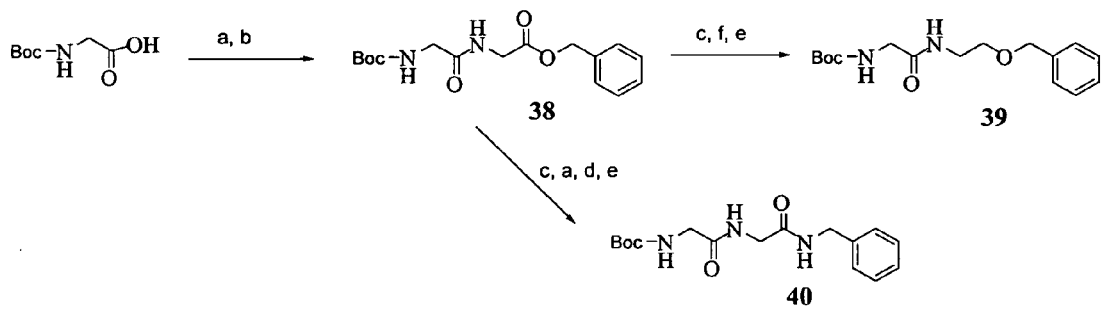

As shown in FIG. 9D (Scheme 6), standard peptide coupling conditions will be used to prepare the diglycyl intermediate (38) from Boc-protected glycine and (O)-benzyl glycine. Intermediate (38) can also be converted into intermediates (39, 40). Reduction over palladium catalyst, followed by LAH/benzylbromide will be used to form the ether intermediate 39. Reduction over palladium catalyst, followed by DCC/HOBT and LAH/benzylbromide will be used to transform the carboxylate into the amide 40.

Intermediates 31-40 will be reacted with yohimbine under standard peptide coupling conditions (as described in Example 1) to form the following monomeric yohimbine derivatives 41-50 as follows: yohimbine benzylurea alkyl amine (41), yohimbine pyrrolidine-2,5-dione alkyl amine (42), yohimbine pyrrolidin-1-yl alkyl amine (43), yohimbine 1H-pyrrol-1-yl alkyl amine (44), yohimbine benzylimidazolidin-2-one alkyl amine (45), yohimbine 1-benzylimidazolidine-2,4-dione alkyl amine (46), yohimbine 3-benzylimidazolidine-2,4-dione alkyl amine (47), yohimbine diglycine benzyl ester (48), yohimbine (benzyloxy)ethylacetamide amine (49), and yohimbine benzyl diacetamide amine (50). These compounds will be tested for antagonist activity and selectivity for the α$_{2c}$-AR as described in the preceding examples.

Although the invention has been described in detail for the purposes of illustration, it is understood that such detail is solely for that purpose, and variations can be made therein by those skilled in the art without departing from the spirit and scope of the invention which is defined by the appended claims.

What is claimed is:

1. A compound according to formula (1)

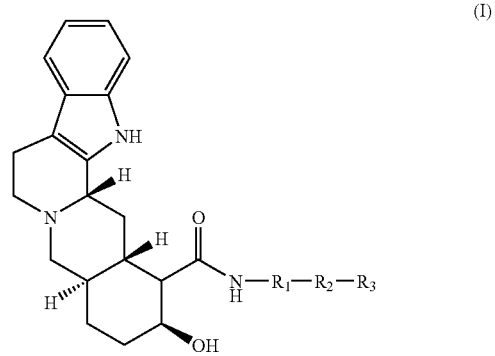

(I)

wherein,

R$_1$ is either a C$_{1-20}$ hydrocarbon, or an aromatic or heteroaromatic ring that is monocyclic or polycyclic;

R$_2$ is optional and is selected from the group of —N(H)— and carbonyl-containing linking groups;

R$_3$ is selected from the group of H, COOH, NH$_2$, a C$_{1-30}$ hydrocarbon, an unsubstituted aromatic or hetero-aromatic ring that is monocyclic or polycyclic, and hydrocarbon-R$_4$ where the hydrocarbon is a C$_{1-30}$ hydrocarbon;

R$_4$ is selected from the group of COOH, NH$_2$, C$_{5-7}$ cycloalkyl, an unsubstituted aromatic or hetero-aromatic ring that is monocyclic or polycyclic, or

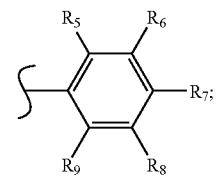

and

R$_5$, R$_6$, R$_7$, R$_8$, and R$_9$ are independently selected from the group of H, C$_{1-6}$ alkyl, halo, C$_{1-2}$ alkylamino, C$_{1-2}$ dialkylamino, amido, C$_{1-2}$ alkylamido, cyano, nitro, C$_{1-6}$ alkoxy, C$_{1-6}$ alcohol, carboxyl containing a C$_{1-6}$ alkyl, carbonyl containing a C$_{1-6}$ alkyl, and an ester containing C$_{1-6}$ alkyl group, provided the compound is not a yohimbine dimer.

2. The compound according to claim 1 wherein the compound is selected from the group of yohimbine monoglycine ester, yohimbine diglycine ester, yohimbine t-butyl carbamate alkyl amine, yohimbine benzyl carbamate alkyl amine, yohimbine alkyl amine, yohimbine benzyl carboxy alkyl amine, yohimbine carboxy alkyl amine, yohimbine benzylurea alkyl amine, yohimbine pyrrolidine-2,5-dione alkyl amine, yohimbine pyrrolidin-1-yl alkyl amine, yohimbine 1H-pyrrol-1-yl alkyl amine, yohimbine benzylimidazolidin-2-one alkyl amine, yohimbine 1-benzylimidazolidine-2,4-dione alkyl amine, yohimbine 3-benzylimidazolidine-2,4-dione alkyl amine, yohimbine diglycine benzyl ester, yohimbine (benzyloxy)ethylacetamide amine, and yohimbine benzyl diacetamide amine.

3. The compound according to claim 1 wherein the compound is selected from the group of yohimbine t-butyl carbamate propyl amine, yohimbine benzyl carbamate propyl amine, yohimbine benzyl carboxy propyl amine, and yohimbine carboxy propyl amine.

4. The compound according to claim 1 wherein $R_1$ is a $C_{2-18}$ straight-chain hydrocarbon.

5. The compound according to claim 4 wherein the $C_{2-18}$ straight-chain hydrocarbon is saturated.

6. The compound according to claim 1 wherein $R_2$ is a carbonyl-containing linking group selected from —C(O)—O—, —N(H)—C(O)—O—, —C(O)—, —N(H)—C(O)—, —N(H)—C(O)—N(H)—,

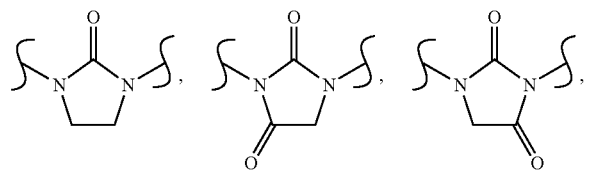

—C(O)—N(H)—$C_{2-10}$ hydrocarbon-O—, —C(O)—N(H)—$C_{2-10}$ hydrocarbon-C(O)—N(H)—, and —C(O)—N(H)—$C_{2-10}$ hydrocarbon-C(O)—O—.

7. The compound according to claim 6 wherein the carbonyl-containing linking group is selected from the group of —C(O)—O—, —N(H)—C(O)—O—, —C(O)—, —N(H)—C(O)—, and —N(H)—C(O)—N(H)—.

8. The compound according to claim 1 wherein $R_3$ is selected from the group of COOH, a $C_{1-30}$ hydrocarbon, and hydrocarbon-$R_4$.

9. The compound according to claim 8 wherein $R_3$ is hydrocarbon-$R_4$ and $R_4$ is COOH or a substituted or unsubstituted phenyl ring.

10. The compound according to claim 1 wherein $R_3$ is an aromatic or hetero-aromatic ring that is monocylic or polycyclic.

11. The compound according to claim 1 in the form of a pharmaceutically acceptable salt.

12. The compound according to claim 1 wherein the compound has at least 10-fold selectivity for an $\alpha_{2c}$-adrenoreceptor over either an $\alpha_{2a}$-adrenoreceptor or an $\alpha_{2b}$-adrenoreceptor.

13. The compound according to claim 1 wherein the compound has at least 25-fold selectivity for an $\alpha_{2c}$-adrenoreceptor over either an $\alpha_{2a}$-adrenoreceptor or an $\alpha_{2b}$-adrenoreceptor.

14. A pharmaceutical composition comprising a compound according to claim 1 and a pharmaceutically acceptable carrier.

15. A method of treating Raynaud's disease comprising:
administering to a patient an effective amount of a compound according to claim 1 under conditions effective to antagonize activity of the $\alpha_{2c}$ adrenergic receptor, thereby treating the Raynaud's disease.

16. The method according to claim 15, wherein the compound is selected from the group of yohimbine t-butyl carbamate propyl amine, yohimbine benzyl carbamate propyl amine, yohimbine benzyl carboxy propyl amine, and yohimbine carboxy propyl amine.

17. The method according to claim 15, wherein said administering is carried out orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes.

18. The method according to claim 15, wherein the effective amount is between about 0.01 to about 100 mg/kg.body wt.

19. A method of antagonizing activity in vitro of an $\alpha_{2c}$ adrenergic receptor comprising:
contacting in vitro an $\alpha_{2c}$ adrenergic receptor with a compound according to claim 1 under conditions effective to antagonize the activity of the $\alpha_{2c}$ adrenergic receptor, wherein the compound selectively antagonizes the $\alpha_{2c}$ adrenergic receptor over other adrenergic receptors.

20. The method according to claim 19, wherein the compound has at least 10-fold selectivity for an $\alpha_{2c}$-adrenoreceptor over either an $\alpha_{2a}$-adrenoreceptor or an $\alpha_{2b}$-adrenoreceptor.

21. The method according to claim 19, wherein the compound has at least 25-fold selectivity for an $\alpha_{2c}$-adrenoreceptor over either an $\alpha_{2a}$-adrenoreceptor or an $\alpha_{2b}$-adrenoreceptor.

22. The method according to claim 19, wherein the compound is selected from the group of yohimbine t-butyl carbamate propyl amine, yohimbine benzyl carbamate propyl amine, yohimbine benzyl carboxy propyl amine, and yohimbine carboxy propyl amine.

* * * * *